US 8,716,013 B2

(12) United States Patent
Despres et al.

(10) Patent No.: US 8,716,013 B2
(45) Date of Patent: *May 6, 2014

(54) RECOMBINANT LENTIVIRAL VECTOR FOR EXPRESSION OF A FLAVIVIRIDAE PROTEIN AND APPLICATIONS THEREOF AS A VACCINE

(75) Inventors: Philippe Despres, La Garenne Colombes (FR); Pierre Charneau, Paris (FR); Frédéric Tangy, Les Lilas (FR); Marie-Pascale Frenkiel, Levallois (FR)

(73) Assignees: Institut Pasteur, Paris (FR); Institut National de la Santé et de la Recherche Médicale, Paris (FR); Centre National de la Recherche Scientifique, Paris (FR)

( * ) Notice: Subject to any disclaimer, the term of this patent is extended or adjusted under 35 U.S.C. 154(b) by 113 days.

This patent is subject to a terminal disclaimer.

(21) Appl. No.: 12/929,215

(22) Filed: Jan. 7, 2011

(65) Prior Publication Data

US 2011/0206710 A1  Aug. 25, 2011

Related U.S. Application Data

(63) Continuation of application No. 11/596,675, filed as application No. PCT/IB2005/001753 on May 16, 2005, now abandoned.

(30) Foreign Application Priority Data

May 17, 2004  (FR) ..................... 04 05366

(51) Int. Cl.
C12N 15/00 (2006.01)
A61K 39/12 (2006.01)

(52) U.S. Cl.
USPC .................. 435/320.1; 424/218.1; 424/207.1

(58) Field of Classification Search
None
See application file for complete search history.

(56) References Cited

U.S. PATENT DOCUMENTS

| | | | |
|---|---|---|---|
| 5,883,081 A | 3/1999 | Kraus et al. |
| 6,498,033 B1 | 12/2002 | Dropulic et al. |
| 6,682,907 B1 | 1/2004 | Charneau et al. |
| 6,870,032 B1 | 3/2005 | Flamand et al. |
| 7,052,830 B1 | 5/2006 | Branch et al. |
| 2003/0104611 A1 | 6/2003 | Johnston et al. |
| 2003/0194392 A1 | 10/2003 | Charneau et al. |
| 2004/0009469 A1 | 1/2004 | Apt et al. |
| 2004/0037848 A1 | 2/2004 | Audonnet et al. |
| 2004/0081636 A1 | 4/2004 | Charneau et al. |
| 2006/0040347 A1 | 2/2006 | Charneau et al. |
| 2006/0073164 A1 | 4/2006 | Tangy et al. |
| 2007/0087354 A1 | 4/2007 | Charneau et al. |
| 2007/0224679 A1 | 9/2007 | Charneau et al. |
| 2009/0214589 A1 | 8/2009 | Despres et al. |
| 2010/0028382 A1 | 2/2010 | Charneau et al. |
| 2010/0221820 A1 | 9/2010 | Charneau et al. |

FOREIGN PATENT DOCUMENTS

| | | | |
|---|---|---|---|
| CA | 2456873 A1 | 8/2004 |
| EP | 1092779 A1 | 4/2001 |
| WO | WO 99/55892 A1 | 11/1999 |
| WO | WO 00/75665 A1 | 12/2000 |
| WO | WO 2004/076619 A2 * | 9/2004 |

OTHER PUBLICATIONS

Monath et al., PNAS, 2006, 103(17):6694-6699.*
Lang et al., Journal of Clinical Virology, 2009, 46(S2):20-24.*
Meunier et al., Journal of Virology, 2008, 82(2):966-973.*
Buffa et al., J. Gen. Virol., 2006, 87:1625-1634.*
Despres et al., J. Infect. Dis., 2005, 191:207-214.*
Singh et al., J. Virology, 1999, 73(6):4823-4828.*
Pletnev et al., "West Nile virus/dengue type 4 virus chimeras that are reduced in neurovirulence and peripheral virulence without loss of immunogenicity or protective efficacy", PNAS, vol. 99, No. 5, pp. 3036-3041 (2002).
Puthenveetil et al., "Successful correction of the human p-thalassemia major phenotype using a lentiviral vector", Blood, vol. 104, No. 12, pp. 3445-3453 (2004).
Ralph et al., "Silencing mutant SOD1 using RNAi protects against neurodegeneration and extends survival in an ALS model", Nature Medicine, vol. 11, No. 4, pp. 429-433 (2005).
Seligman et al., "Live *Flavivirus* vaccines: reasons for caution", The Lancet, vol. 363, pp. 2073-2075 (2004).
Shrestha et al., "Role of CD8*T Cells in Control of West Nile Virus Infection", Journal of Virology, vol. 78, No. 15, pp. 8312-8321 (2004).
Sirven et al., "The human immunodeficiency virus type-1 central DNA flap is a crucial determinant for lentiviral vector nuclear import and gene transduction of human hematopoietic stem cells", Blood, vol. 96, No. 13, pp. 4103-4110 (2000).
Takahashi et al., "Rescue from Photoreceptor Degeneration in the rd Mouse by Human Immunodeficiency Virus Vector-Mediated Gene Transfer", Journal of Virology, vol. 73, No. 9, pp. 7812-7816 (1999).
Tonry et al., "Persistent Shedding of West Nile Virus in Urine of Experimentally Infected Hamsters", Am. J. Trop. Med. Hyg., vol. 72, No. 3, pp. 320-324 (2005).

(Continued)

*Primary Examiner* — Stacy B. Chen
(74) *Attorney, Agent, or Firm* — Law Office of Salvatore Arrigo and Scott Lee, LLP

(57) ABSTRACT

Use of a recombinant lentiviral vector comprising a polynucleotide fragment encoding at least one protein of a virus of the family Flaviviridae or an immunogenic peptide of at least 8 amino acids of said protein, for preparing a pharmaceutical composition intended for the prevention and/or the treatment of a Flaviviridae infection in a sensitive species.

14 Claims, 7 Drawing Sheets

(56) References Cited

OTHER PUBLICATIONS

Vandendriessche et al., Lentiviral vectors containing the human immunodificency virus type-1 central polypurine tract can efficiently transduce nondividing hepatocytes and antigen-presenting cells in vivo, Blood, vol. 100, No. 3, pp. 813-822 (2002).

Wang et al., "Immunization of Mice Against West Nile Virus with Recombinant Envelope Protein", The Journal of Immunology, vol. 167, pp. 5273-5277 (2001).

Yee et al., "A general method for the generation of high-titer, pantropic retroviral vectors: Highly efficient infection of primary hepatocytes", P.N.A.S., USA, vol. 91, pp. 9564-9568 (1994).

Zarei, et al., "Lentiviral Transduction of Dendritic Cells Confers Protective Antiviral Immunity in Vivo", Journal of Virology, vol. 78, No. 14, pp. 7843-7845 (2004).

Zennou et al., "HIV-1 Genome Nuclear Import Is Mediated by a Central DNA Flap", Cell, vol. 101, pp. 173-185 (2000).

Zennou et al., "The HIV-1 DNA flap stimulates HIV vector-mediated cell transduction in the brain", Nature Biotechnology, vol. 19, pp. 446-450 (2001).

Zufferey et al., "Multiply attenuated lentiviral vector achieves efficient gene delivery in vivo", Nature Biotechnology, vol. 15, pp. 871-875 (1997).

Bartosch et al.; "Infectious Hepatitis C Virus Pseudo-Particles Containing Functional E1-E2 Envelope Proteins Complexes"; J.Exp. Med, vol. 197, No. 5, pp. 6333-642, (2003).

Colombage et al.; "DNA-Based and Aplha Virus-Vectored Immunisation With PrM and E Protein Elicits Long-Lived and Protective Immunity Against the *Flavivirus*, Murray Valley Encephalitis Virus"; Virology, vol. 250, pp. 151-163, (1998).

Malkinson et al., Emerging Infectious Diseases, 2002, 8(4):392-397.

Iglesias et al.; "A Single Immunization With a Minute Dose of a Lentiviral Vector-Based Vaccine Is Highly Effective At Eliciting Protective Humoral Immunity Against West Nile Virus"; The Journal of Gene Medicine, vol. 8, No. 3, pp. 265-274, (2003).

Despres et al.; "Live Measles Vaccine Expressing the Secreted Form of the West Nile Virus Envelope Glycoprotein Protects Against West Nile Virus Encephalitis"; Journal of Infectious Diseases, vol. 191, No. 2, pp. 207-214, (2005).

Zarei et al.; "Lentiviral Transduction of Dendritic Cells Confers Protective Antiviral Immunity In Vivo"; Journal of Virology, vol. 78, No. 14, pp. 7843-7845, (2004).

He et al.; "Immunization With Lentiviral Vector-Transduced Dendritic Cells Induces Strong and Long-Lasting T Cell Responses and Therapeutic Immunity"; Journal of Immunology, vol. 174, No. 6, pp. 3808-3817, (205).

Wang et al.; "Immunization of Mice Against West Nile Virus With Recombinant Envelope Protein"; Journal of Immunology, vol. 167, pp. 5273-5277, (2001).

Wiznerowicz et al.; "Harnessing HIV for Therapy, Basic Research and Biotechnology"; Trends in Biotechnology, vol. 23, No. 1, pp. 42-47, (2005).

Despres et al., "Live Measles Vaccine Expressing the Secreted Form of the West Nile Virus Envelope Glycoprotein Protects against West Nile Virus Encephalitis", Journal of Infectious Diseases, vol. 191, pp. 207-214 (2005).

Rohrlich et al., "Use of a Lentiviral Vector Encoding a HCMV-Chimeric IE1-pp65 Protein for Epitope Identification in HLA-Transgenic Mice and for ex vivo Stimulation and Expansion of CD8. Cytotoxic T Cells From Human Peripheral Blood Cells", Human Immunology, vol. 65, pp. 514-522 (2004).

Daupin et al. Vaccine, 2007, vol. 25, p. 5563-5576.

Berthet et al. Journal of General Virology, 1997, vol. 78, p. 2293-2297.

Arroyo et al., "ChimeriVax-West Nile Virus Live-Attenuated Vaccine: Preclinical Evaluation of Safety, Immunogenicity, and Efficacy", Journal of Virology, vol. 78, No. 22, pp. 12497-12507 (2004).

Beasley et al., "Identification of Neutralizing Epitopes within Structural Domain III of the West Nile Virus Envelope Protein", Journal of Virology, vol. 76, No. 24, pp. 13097-13100 (2002).

Benhamida, et al., "Transduced CD34" Cells from Adrenoleukodystrophy Patients with HIV-Derived Vector Mediate Long-Term Engraftment of NOD/SCID Mice, Molecular Therapy, vol. 7, No. 3, pp. 317-324 (2003).

Ben-Nathan et al., "Prophylactic and Therapeutic Efficacy of Human Intravenous Immunoglobulin in Treating West Nile Virus Infection in Mice", The Journal of Infectious Disease, vol. 188, pp. 5-12 (2003).

Biffi et al., "Correction of metachromatic leukodystrophy in the mouse model by transplantation of genetically modified hematopoietic stem cells", The Journal of Clinical Investigation, vol. 113, No. 8, pp. 1118-1129 (2004).

Breckpot et al., "Lentivirally transduced dendritic cells as a tool for cancer immunotherapy", The Journal of Gene Medicine, vol. 5, pp. 654-667 (2003).

Brussel et al., "Analysis of Early Human Immunodeficiency Virus Type 1 DNA Synthesis by Use of a New Sensitive Assay for Quantifying Integrated Provirus", Journal of Virology, vol. 77, No. 18, pp. 10119-10124 (2003).

Ceccaldi et al., "New insights on the neuropathogenicity of West Nile virus", FEMS Microbiology Letters, vol. 233, pp. 1-6 (2004).

Charrel et al., "Evolutionary relationship between Old World West Nile virus strains Evidence for viral gene flow between Africa, The Middle East, and Europe", Virology, vol. 315, pp. 381-388 (2003).

Dauphin et al., "West Nile: worldwide current situation in animals and humans", Comp. Immun. Microbiol. Infect. Dis., vol. 27, pp. 343-355 (2004).

Davis et al., "West Nile Virus Recombinant DNA Vaccine Protects Mouse and Horse from Virus Challenge and Expresses In Vitro a Noninfectious Recombinant Antigen That Can Be Used in Enzyme-Linked Immunosorbent Assays", Journal of Virology, vol. 75, No. 9, pp. 4040-4047 (2001).

Despres et al., "Differences between Cell Membrane Fusion Activities of Two Dengue Type-1 Isolates Reflect Modifications of Viral Structure", Virology, vol. 196, pp. 209-219 (1993).

Despres et al., "Effects of Anti-E2 Monoclonal Antibody on Sindbis Virus Replication in AT3 Cells Expressing bcl-2", Journal of Virology, vol. 69, No. 11, pp. 7006-7014 (1995).

Esslinger et al., "In vivo administration of a lentiviral vaccine targets DCs and induces efficient CD8+ T cell responses", The Journal of Clinical Investigation, vol. 111, No. 11, pp. 1673-1681 (2003).

Firat et al., "Use of lentiviral flap vector for induction of CTL immunity against melanoma. Perspectives for immunotherapy", The Journal of Gene Medicine, vol. 4, pp. 38-45 (2002).

Giannini et al., "A Highly Efficient, Stable, and Rapid Approach for Ex Vivo Human Liver Gene Therapy Via a FLAP Lentiviral Vector", Hepatology, vol. 38, No. 1, pp. 114-122 (2003).

Gould et al., "Evolution and dispersal of encephalitic *Flaviviruses*", Archives of Virology Suppl, vol. 18, pp. 65-84 (2004).

Hacein-Bey-Abina et al., "LMO2-Associated Clonal T Cell Proliferation in Two Patients after Gene Therapy for SCID-X1", Science, vol. 302, pp. 415-419 (2003).

Kootstra et al., "Efficient Production of Human FVIII in Hemophilic Mice Using Lentiviral Vectors", Molecular Therapy, vol. 7, No. 5, pp. 623-631 (2003).

Kordower et al., "Neurodegeneration Prevented by Lentiviral Vector Delivery of GDNF in Primate Models of Parkinson's Disease", Science, vol. 290, pp. 767-773 (2000).

Lanciotti et al., "Complete Genome Sequences and Phylogenetic Analysis of West Nile Virus Strains Isolated from the United States, Europe, and the Middle East", Virology, vol. 298, pp. 96-105 (2002).

Lucas et al., "The Israeli strain IS-98-STI of West Nile virus as viral model for West Nile encephalitis in the Old World", Virology Journal, vol. 1, No. 9 (2004).

Mashimo et al., "A nonsense mutation in the gene encoding 2'-5'-oligoadenylate synthetase/L1 isoform is associated with West Nile virus susceptibility in laboratory mice", P.N.A.S., vol. 99, No. 17, pp. 11311-11316 (2002).

Metharom et al., "Lentiviral Vector-Mediated Tyrosinase-Related Protein 2 Gene Transfer to Dendritic Cells for the Therapy of Melanoma", Human Gene Therapy, vol. 12, pp. 2203-2213 (2001).

(56) References Cited

OTHER PUBLICATIONS

Minke et al., "Recombinant canarypoxvirus vaccine carrying the prM/E genes of West Nile virus protects horses against a West Nile virus-mosquito challenge", Archives of Virology Suppl, vol. 18, pp. 221-230 (2004).

Nguyen et al., "Highly Efficient Lentiviral Vector-Mediated Transduction of Nondividing, Fully Reimplantable Primary Hepatocytes", Molecular Therapy, vol. 6, No. 2, pp. 199-209 (2002).

Nusbaum et al., "Absence of Humoral Response in Flamingos and Red-Tailed Hawks to Experimental Vaccination with a Killed West Nile Virus Vaccine", Avian Diseases, vol. 47, pp. 750-752 (2003).

Palmowski et al., Intravenous Injection of a Lentiviral Vector Encoding NY-ESO-1 Induces an Effective CTL Response, The Journal of Immunology, vol. 172, pp. 1582-1587 (2004).

Pawliuk et al., "Correction of Sickle Cell Disease in Transgenic Mouse Models by Gene Therapy", Science, vol. 294, pp. 2368-2371 (2001).

* cited by examiner

| Vector | Anti-WNV[1] antibody titre | TNRF$_{90}$[2] |
|---|---|---|
| TRIPΔU3.CMV-GFP | | |
| D + 14[3] | < 100 | < 10 |
| D + 23[4] | < 100 | < 10 |
| TRIPΔU3.CMV-Es (WNV) | | |
| D + 14[3] | 10 000 | 10 |
| D + 23[4] | 20 000 | 20 |

[1] ELISA assay using purified WN virus as antigen.

[2] Titre of antibodies that neutralize 90% of the infectious foci of the WN virus.

[3] Sera taken after 14 days of immunization.

[4] Sera taken after 23 days of immunization.

Figure 2

Immunization: 15 days
Viral challenge: 10 LD50s

Immunization: 30 days
Viral challenge: 100 LD50s

A.

Pre challenge antisera to TRIP/WNsE

Control sera | Antisera to TRIP/GFP | Day 6 | Day 13 | Day 20 | Day 27

← E

B.

Anti-WNV HMAF | Post-challenge antisera to TRIP/WNsE

Antisera to MV | No virus | WNV | Day 7 | Day 14 kDa
84 –
53 –      ← E
35 –
28 –      ← prM
20 –

Figure 6

RECOMBINANT LENTIVIRAL VECTOR FOR EXPRESSION OF A FLAVIVIRIDAE PROTEIN AND APPLICATIONS THEREOF AS A VACCINE

This application is a continuation of U.S. application Ser. No. 11/596,675, filed on Aug. 4, 2008 (now abandoned), which was the National Stage of International Application PCT/IB2005/001753, filed May 16, 2005, which claims the benefit of Appln. FR 0405366, filed on May 17, 2004, in France.

The claimed invention was made as a result of activities undertaken within the scope of a Joint Research Agreement between Institut Pasteur and Centre National de la Recherche Scientifique, as a result of activities undertaken within the scope of that Agreement. The Agreement was in effect prior to the date of the invention.

The present invention relates to a recombinant lentiviral vector for expression of a protein of a Flaviviridae and to its applications as a vaccine intended for the prevention and/or treatment of an infection with a virus of the family Flaviviridae, in a sensitive species (host or reservoir).

The family Flaviviridae is divided up into three genera: Flavivirus, Pestivirus and Hepacivirus or hepatitis C virus; Flaviviridae represent a major human and veterinary health problem due to the large number of both human and veterinary diseases induced by Flaviviridae. Specifically, there are, for example, more than 70 species of Flavivirus, at least 50% of which are the cause of human or veterinary diseases.

Flaviviridae are small enveloped viruses. Their genome is a single-stranded RNA molecule of positive polarity, of 9.5 kb to 12.5 kb, depending on the Flaviviridae, and contains a single open reading frame flanked by two short non-coding regions at its 5' and 3' ends. This open reading frame is translated into a polyprotein, which is the precursor of the structural proteins, in its N-terminal portion, and of the non-structural (NS) proteins, in its C-terminal portion.

More precisely:

for the Flaviviruses, the genome is a single-stranded RNA molecule of positive polarity, of approximately 10-12 kbases. The genomic RNA is combined with several copies of the capsid protein C so as to form the nucleocapsid; it is surrounded by a viral envelope consisting of a double lipid layer derived from the endoplasmic reticulum (ER) membranes, in which the envelope protein E and the membrane protein M are anchored. The Flavivirus genomic RNA contains a single open reading frame of approximately 10 500 nucleotides, flanked by two short non-coding regions at its 5' and 3' ends. The genome is translated into a polyprotein of approximately 3400 amino acids, which is the precursor of the three structural proteins C, prM (intracellular precursor of M) and E, in its N-terminal portion, and of at least five non-structural (NS) proteins NS1 to NS5, in its C-terminal portion. The following structure is therefore observed: C-prM/M-E-NS1-NS2A/2B-NS3-NS4A/4B-NS5, for the Pestiviruses, the genomic RNA is longer than 12 kbases, and contains a single open reading frame translated into a polyprotein of approximately 3900 amino acids, which is the precursor of 11 to 13 pestiviral proteins, four of which are structural proteins: the following structure is observed: $N^{pro}$-$C^{ems}$-E1-E2-p7-NS2-NS3-NS4A/4B-NS5A/5B and for the Hepaciviruses, the genomic RNA comprises approximately 9.5 kbases, and contains a single open reading frame translated into a polyprotein of approximately 3000 amino acids, which is the precursor of the three structural proteins C, E1 and E2, in its N-terminal portion, and of at least seven non-structural (NS) proteins NS1 to NS5, in its C-terminal portion. The following structure is observed: C-E1-E2-NS1-NS2-NS3-NS4A/4B-NS5A/5B.

Many serious human and animal pathologies are induced by the viruses of this family; according to the infecting virus, the various symptoms observed are generally fever (cyclic or non-cyclic), haemorrhagic fever, diarrhoea, encephalitis, hepatitis or septic shock. More precisely, the various viruses in question are the following:

Flaviviruses: the majority of Flaviviruses are transmitted to the vertebrate host by mosquitoes (*Culex, Aaedes, Anopheles* or *Mansonia*) or ticks: (i) viruses transmitted by mosquitoes: dengue virus (types 1 to 4), yellow fever virus (YFV), Japanese encephalitis virus (JEV), West Nile virus (WNV), Murray Valley encephalitis virus (MVEV), Saint-Louis encephalitis virus (SLEV) and (ii) viruses transmitted by ticks: tick-borne encephalitis virus (TBEV), Kyasanur forest disease virus, Omsk haemorrhagic fever virus and Louping ill virus.

Pestiviruses: border disease virus (BDV), bovine viral diarrhoea virus (BVDV) and classical swine fever virus (CSFV) or hog cholera virus.

Hepaciviruses: hepatitis C virus and hepatitis G virus.

Migratory birds can be the reservoir of some of these viruses, in particular the West Nile virus, which has also been noted to cross the species barrier, in horses and humans.

A certain number of vaccine strategies have been proposed to date (Gould E A: *Flavivirus Infections in Humans, Encyclopaedia of Life Sciences*, 2001; Pugazchev K V et al., *Internat. J. Parasitol*, 2003, 33, 567-582; Putnak R et al., *Advances in Virus Research* 2003, 61, 445-468; Smith D B, *Hepatitis C virus, Encyclopaedia of Life Sciences*, 2001) and relate to:

vaccines containing live attenuated viruses or inactivated viruses (Pugachev K V et al., 2003, mentioned above; Gould E A, 2001, mentioned above; Brinton M A, Annu. Rev. Microbiol., 2002, 56, 371-402; Hamers C. et al., Vet. Rec., 2003, 153, 8, 236-240; Kovacs F. et al., Vet. Microbiol., 2003, 96, 2, 117-131);

vaccines containing viral subunits;

vaccines containing one or more virus-derived antigens (Wang T et al., J. Immunol., 2001, 167, 5273-5277);

vaccines containing chimeric viruses (Pugachev K V et al., 2003, mentioned above); or DNA vaccines (Putnak R et al., 2003, mentioned above; Turell M J et al., *Emerging Infectious Diseases*, 2003, 9, 9, 1077-1081; Davis B S et al., J. Virol., 2001, 4040-4047; Pan C H et al., J. Virol., 2001, 75, 23, 11457-11463); these vaccines use various vectors. In particular, Putnak R et al., 2003, mentioned above, specifies that, for optimum expression, the most appropriate regulatory elements should be chosen (promoter and enhancer); in general, at the very least for the Flaviviruses, it is recommended to use plasmid vectors comprising a CMV promoter (plasmid pcDNA3, Invitrogen, for example) or RSV promoter and coexpressing the prM and E genes and, optionally, also at least one non-structural protein.

Taking, for example, WNV, the emergence of which in the northern hemisphere, and in particular in the United States, is quite recent, the various vaccine strategies currently proposed to combat West Nile virus infection are as follows:

Japanese encephalitis virus produced in mouse brain, inactivated with formol (JE-VAX®, Aventis-Pasteur; Monath et al., Curr. Drug Targets Infect. Disord., 2001, 1, 37-50); the existence of a cross protection capable of protecting humans or horses against West Nile viral infection has not been demonstrated and is controversial (Monath, A M; Trop. Med. Hyg., 2002, 66, 113-114). In addition, studies in mice have shown that cross immunity could induce brain inflammation during West Nile infection;

formol-inactivated West Nile virus (International Application WO 03/061555); this vaccine proposed for the immunization of horses has been found to be devoid of any pathogenic effect and effective against West Nile virus infection in horses; however due to the low magnitude humoral response, several injections, followed by annual boosts are required;

chimeric virus derived from the attenuated strain of the yellow fever virus (strain 17D; ChimeriVax™-WN); more precisely, the ChimeriVax®-West Nile chimeric virus contains the prM-E cassette of WNV strain New York 1999, in the attenuated virus YV 17D (International Application WO 03/059384 and Pletnev A G et al., PNAS, 2002, 99, 5, 3036-3041; Monath T P et al., *Curr. Drug Targets Disord.*, 2001, 1, 1, 37-50); the prM and E genes of the West Nile virus are inserted into the yellow fever virus or the dengue virus, which therefore serve as vector. The genes encoding the nucleocapsid protein and the non-structural proteins, and also the non-translated terminal regions that originate from strain 17D or from DEN4, are used for replication of the recombinant chimeric virus. The chimeric viruses replicate in the host like the 17D or DEN4 virus, but immunize specifically against the West Nile virus (Monath et al., Curr. Drug Targets Infect. Disord., mentioned above). Infection with the chimeric virus stimulates the various pathways of the immune response. In addition, the chimeric viral particles contain the complete E protein, which has redundant neutralizing epitopes. Thus, replication of the chimeric virus in the host induces high titres of neutralizing antibodies that prevent early dissemination of the virus, and the cytotoxic T immunity eliminates the virus that has succeeded in infecting cells. The post-infection memory response, which is rapid and stronger than the post-vaccine response, also contributes to the protection against West Nile infection. It has been shown that prior immunization with the 17D strain does not inhibit infection with the chimeric virus but, on the contrary, it increases the production of specific antibodies. It has also been shown, in mice and non-human primates, that the ChimeriVax™-JE chimeric vaccine is less neurovirulent than the 17D strain. In addition, the genome of the chimeric virus is stable over repeated passages in vivo and in cell culture. The ChimeriVax™-WN chimeric viruses are derived from a vaccine strain that has proved its innocuousness and its effectiveness in humans since it was developed for human immunization more than 65 years ago, and used in several hundred million individuals (Monath et al., Curr. Drug Targets Infect. Disord., mentioned above); however the use of chimeric live-attenuated virus raises safety concerns; non-homologous recombination between different species is possible as demonstrated by naturally occurring recombinant flaviviruses (Seligman S J and Gould E A, Lancet, 2004, 363, 2073-2075).

naked DNA (Davis et al., J. Virol., 2001, 75: 4040-4047; Turell et al., Emerg. Infect. Diseases, 2003, 9, 1077-1081 and International Application WO 03/061555); the naked DNA vector used is a vector pCBWN comprising the cytomegalovirus early promoter, a sequence encoding a signal peptide, derived from the Japanese encephalitis virus, and the sequences encoding the prM and E proteins of the West Nile virus. It has been shown that a simple intramuscular injection of this plasmid induces protective immunity against West Nile infection, in mice and horses;

recombinant protein E (Wang et al., J. Immunol., 2001, 167, 5273-5277); the complete E protein or the E protein from which the C-terminal region has been deleted (residues E1 to E409), expressed in the form of a fusion protein in *E. coli* and purified by affinity chromatography, induces the production of neutralizing antibodies directed against the E protein, in mice. The soluble E protein, from which the C-terminal region has been deleted, induces complete protection in mice, whereas only partial protection is observed with the complete E protein.

Even though most of the vaccines currently proposed are effective overall, there is nevertheless still a need for new preventive measures, and especially in the field of DNA vaccines with respect to Flaviviridae; in particular, there exists a real need for vectors that are useful both in the prevention of diseases induced by these viruses in human medicine and veterinary medicine, and in the eradication of these viruses in the reservoirs.

In fact, in the case of Hepaciviruses, for example, and more particularly of hepatitis C, trials aimed at protecting patients suffering from hepatitis C fail because the vaccinia virus is used to express the HCV viral proteins; now, this virus causes splicing which results in truncated viral proteins whose protective effectiveness is reduced (Dumonceaux J. et al., J. Virol., 2003, 77, 24, 13418-13424).

In addition, there is still a need for vaccines that only require few injections (one or two at most), so as to facilitate their use, in particular in countries where it is difficult to set up immunization programmes that are followed.

Surprisingly, the inventors have shown that a recombinant lentiviral vector for expression of at least one immunogenic protein of a virus of the family Flaviviridae effectively makes it possible to induce a strong immune response in the individual (human or animal) immunized, capable in particular of protecting said individual against infection with this virus.

The recombinant lentiviral vector was able to induce a very early, long-lasting, fully protective immune response against a high dose West Nile virus challenge.

The inventors provide the first evidence that lentiviral vectors are efficient tools for eliciting a humoral protective response against a pathogen. This broadens the applicability of lentiviral vectors as vaccination tools against pathogens like viruses of the Flaviviridae family, in which a neutralizing humoral response is one active arm of the immune system.

Consequently, a subject of the present invention is the use of a recombinant lentiviral vector comprising a polynucleotide fragment encoding at least one protein of a virus of the family Flaviviridae or an immunogenic peptide of at least 8 amino acids of said protein, for preparing an immunogenic composition intended for the prevention and/or the treatment of a Flaviviridae infection in a sensitive species.

Such a vector has a certain number of advantages and is particularly suitable for the needs disclosed above:

it has an increased immunogenic capacity; consequently, it is effective after a single administration in the sensitive species. The effectiveness of this vector is related at once: (i) to its tropism for antigen-presenting cells, or APCs, such as dendritic cells, in particular when it is injected subcutaneously, (ii) to the stable integration, into the cellular genome, of the sequences of interest carried by these vectors, which allows long-lasting expression of the antigen in vivo, in particular in dendritic cells, and (iii) to its ability to stimulate the dendritic cell-dependent immune response. Thus, the duration of expression of the antigen in the dendritic cells, which is greater than that usually obtained with pulsed dendritic cells, advantageously makes it possible to do away with repeated administration of the vector, it is non-replicative; consequently, it has little or no pathogenic capacity in the sensitive species and no infectious capacity, i.e. no risk of dissemination in the environment, it is non-tumorigenic; it results in stable integration of the sequence of interest in the genome of the host cell, without causing any tumorigenic effect, it exhibits no species restriction and has a broadened cellular tropism, in particular due to the fact that it is possible to produce pseudotypes with envelope proteins from other viruses, such as the glycoproteins G of the vesicular stomatitis virus (VSV), of viruses of the family Rhabdoviridae, for instance the rabiesvirus, and of the ebola virus; consequently, it is effective for preventive and/or curative immunization in any sensitive species, and it makes it possible to do away with the use of adjuvants.

Definitions polynucleotide fragment: the term "poly-nucleotide fragment or polynucleotide" is intended to mean a DNA or RNA fragment of at least 24 bases or base pairs, preferably from 24 to 5000 bases or base pairs, in particular a cDNA or cDNA fragment.

immunogenic fragment: a peptide fragment capable of inducing a specific humoral and/or cellular response in a species sensitive to infection with a Flaviviridae.

polynucleotide fragment encoding at least one protein of a Flaviviridae or an immunogenic peptide of at least 8 amino acids of said protein: a polynucleotide as defined above, encoding one or more structural or non-structural proteins and/or one or more immunogenic fragments of Flaviviridae. The open reading frame (ORF) of the Flaviviridae polyprotein and the coding sequences of the various Flaviviridae proteins which are included in said ORF are known to those skilled in the art and accessible, either in the databases, in particular that of the NCBI (http://www.ncbi.nlm.nih.gov), or in reference works, for instance *Virus Taxonomy. Classification and nomenclature of viruses. Sixth report of the International Committee on taxonomy of viruses* (F. A. Murphy et al., *Archives of Virology Supplement* 10, 1995, Springer Verlag, Vienna, N.Y.). The invention encompasses the coding sequences of any Flaviviridae and the variants derived by mutation (insertion, deletion, substitution) of one or more nucleotides of said coding sequence or by a shift in the open reading frame of one or two nucleotides (ORF+1 and ORF+2), provided that said mutations do not substantially modify the antigenic and/or immunogenic properties of said protein or of said fragment. The invention encompasses in particular the variant polynucleotides derived from the above by mutation (insertion, deletion, substitution) of nucleotides, provided that the modified nucleotide fragments conserve, under high stringency hybridization conditions, an ability to specifically hybridize with the modified polynucleotides from which they derive.

high stringency hybridization conditions: for the purpose of the present invention, the expression "high stringency hybridization conditions" is intended to mean conditions of temperature and of ionic strength that are chosen such that they make it possible to maintain the specific and selective hybridization between complementary polynucleotides. By way of illustration, high stringency conditions for the purposes of defining the polynucleotides above are advantageously as follows: the DNA-DNA or DNA-RNA hybridization is carried out in two steps: (1) prehybridization at 42° C. for 3 hours in phosphate buffer (20 mM, pH 7.5) containing 5×SSC (1×SSC corresponds to a solution of 0.15 M NaCl+0.015 M sodium citrate), 50% of formamide, 7% of sodium dodecyl sulphate (SDS), 10×Denhardt's, 5% of dextran sulphate and 1% of salmon sperm DNA; (2) hybridization for 20 hours at 42° C., followed by 2 washes of 20 minutes at 20° C. in 2×SSC+2% SDS, 1 wash of 20 minutes at 20° C. in 0.1×SSC+0.1% SDS. The final wash is carried out in 0.1×SSC+0.1% SDS for 30 minutes at 60° C.

sensitive species: the expression "species sensitive to infection with a Flaviviridae" is intended to mean both a host species capable of developing a pathology induced by a Flaviviridae, such as a human or non-human mammal, and a reservoir species responsible for propagation of the virus without the development of symptoms, such as in particular a bird or a reptile (crocodile).

recombinant lentiviral vector: the term "recombinant lentiviral vector" is intended to mean both an isolated nucleic acid molecule corresponding to the recombinant genome of a lentiviral vector, in particular included in a plasmid (vector plasmid), and a recombinant lentiviral particle (vector particle) that includes said recombinant genome, produced in a suitable cellular system, optionally pseudotyped with envelope proteins from other viruses such as the glycoproteins G of the vesicular stomatitis virus (VSV), of the rabiesvirus and of the ebola virus.

In accordance with the invention, said lenti-viral vector is selected from the group consisting of those derived from: HIV (human immunodeficiency virus), for example HIV-1 or HIV-2, CAEV (caprine arthritis encephalitis virus), EIAV (equine infectious anaemia virus), VMV (visna/maedi virus), SIV (simian immuno-deficiency virus) or FIV (feline immunodeficiency virus). The invention also encompasses the chimeric lentiviruses derived from at least two different lentiviruses. The choice of the lentiviral vector depends in particular on the sensitive species; for example, vectors derived from HIV are advantageously used for human immunization.

The lentiviral vectors are known to those skilled in the art; they consist of a recombinant nucleotide sequence (recombinant lentiviral genome) comprising: (i) a sequence of interest (coding sequence of Flaviviridae, in the case of the present invention) placed under the control of regulatory signals for transcription and for expression, and (ii) the regulatory sequences of lentiviral origin necessary and sufficient for encapsidation, reverse transcription and viral integration, and, optionally, regulatory sequences for the Rev protein (RRE or rev responsive element). Mention may in particular be made of lentiviral vectors derived from HIV, described by Poznansky et al. (J. Virol., 1991, 65, 532-536) and Naldini et al. (Science, 1996, 272, 263-267) or from FIV, described by Poeschla et al. (Nature Medicine, 1998, 4, 354-357), and also the minimal vectors derived from the above, as described in International Applications WO 99/32646 and WO 98/17815.

In accordance with the invention, said lenti-viral vectors are vectors capable of expressing the coding sequence(s) as defined above, in a suitable cellular system; said vector comprises an expression cassette that includes the suitable regulatory elements for transcription (promoter, enhancer, Kozak consensus sequence, polyadenylation signal, etc.) under the control of which are inserted the coding sequences as defined above; said coding sequences of interest comprise the signals required for cell transport, for instance a signal for translocation in the endoplasmic reticulum, derived in particular from the ORF preceding said coding sequence in the polyprotein of said Flaviviridae. For example, in the case of the Flaviviruses, when said coding sequence is that of the E protein or of a fragment of said protein, said signal sequence is advantageously derived from the M protein precursor (prM). Advantageously, said expression cassette comprises a strong ubiquitous promoter such as the cytomegalovirus (CMV) early promoter or an enhancer free promoter such as the elongation factor 1α (EF1α) or the phosphoglycerate (PGK) promoters.

In addition, said vector may also comprise a suicide gene such as herpes type 1 thymidine kinase (HSV 1-TK), so as to eliminate the transduced cells by treatment with the appropriate drug, for example acyclovir in the case of HSV 1-TK.

The invention encompasses simple expression vectors and multiple expression vectors that allow simultaneous expression of several coding sequences from the same promoter or from different promoters, said promoters being located in the same region or else in different regions of said expression vector.

According to an advantageous embodiment of said use, said recombinant lentiviral vector is of triplex type.

The vectors of triplex type are in particular described in Zennou et al., Cell, 2000, 101, 173-185 and in International Applications WO 99/55892, WO 01/27304 and WO 01/27300.

The triplex vectors are characterized in that they comprise a DNA region capable of forming a triplex (or DNA trimer) during viral reverse transcription. This triplex DNA region consists of a cis-active region for central initiation, or polypurine tract (cPPT), and a cis-active region for termination (CTS), said regions making it possible to initiate the transcription of a + strand whose synthesis is initiated by the PTT region present at the centre of the genome of the lentivirus, and to interrupt the transcription of a + strand whose synthesis is initiated at a 3' PPT site upstream of the retroviral LTR. The presence of this triplex DNA region in the lentiviral vectors notably improves the transduction of genes in mitotic or non-mitotic cells, by stimulating the rate of nuclear import of the vector.

According to another advantageous embodiment of said use, said recombinant lentiviral vector comprises a 3' LTR in which the promoter and the activator have been deleted from the U3 region; this deletion provides additional safety features.

According to another advantageous embodiment of said use, said recombinant lentiviral vector is pseudotyped with at least one envelope protein of another virus, preferably the vesicular stomatitis virus (VSV) glycoprotein G; the VSV glycoprotein G advantageously makes it possible to obtain high titres of vector particles and to produce vector particles having a broad cellular tropism, capable of transducing in particular antigen-presenting cells such as dendritic cells, in any vertebrate species: humans or animals including horses, fowl, and zoo animals at risk.

In accordance with the invention, said Flaviviridae is chosen from a Flavivirus, a Pestivirus or a Hepacivirus, as specified above.

According to yet another advantageous embodiment of said use, said Flaviviridae is selected from the group consisting of the West Nile virus, dengue virus, yellow fever virus and hepatitis C virus.

In accordance with the invention, said polynucleotide, in particular a cDNA or a cDNA fragment of Flaviviridae encodes: (i) one or more different structural proteins (C, prM, M, E, E1, E2), and/or (ii) one or more different non-structural (NS) proteins, and/or (iii) one or more different immunogenic fragments of said proteins, said proteins or their fragments being derived either from the same Flaviviridae (monovalent vaccine) or from various Flaviviridae and/or from different serotypes or different types of the same Flaviviridae, for preparing polyvalent vaccines.

Said cDNA can also derive from a coding sequence of a Flaviviridae by a shift in the open reading frame of one or two nucleotides (ribosomal frameshifting). Such cDNAs are known to those skilled in the art, in particular for the C protein of the hepatitis C virus (Xu et al., EMBO, 2001, 20, 3840-3848; Roussel et al., J. Gen. Virol., 2003, 84, 1751-1759; Vassilaki et al., J. Biol. Chem., 2003, 278, 40503-40513; International Application WO 99/63941).

According to yet another advantageous embodiment of said use, said polynucleotide is a fragment of a coding sequence of Flaviviridae corresponding to the accession number in the NCBI database listed in Table 1:

TABLE 1

Coding sequences of Flaviviridae

| FLAVIVIRIDAE | NCBI accession number | Sequence description |
|---|---|---|
| Flavivirus | M23027 | 5' cDNA sequence of the polyprotein of the dengue virus type 1 |
| Flavivirus | M19197 | DNA equivalent of the genome of the dengue virus type 2 |
| Flavivirus | M93130 | DNA equivalent of the genome of the dengue virus type 3 |
| Flavivirus | M14931 | DNA equivalent of the genome of the dengue virus type 4 |
| Flavivirus | M12294 | DNA equivalent of the genome of the West Nile virus |
| Flavivirus | AF481864 | DNA equivalent of the genome of the IS-98-ST1 strain of the West Nile virus |
| Flavivirus | M18370 | DNA equivalent of the genome of the Japanese encephalitis virus |
| Flavivirus | X03700 | cDNA of the polyprotein of the yellow fever virus (vaccination strain 17D) |
| Flavivirus | U27495 | DNA equivalent of the genome of the Neudoerfl virus of the tick-borne encephalitis virus complex (TBE complex) |
| Flavivirus | M73835 | cDNA of the structural proteins of the Langat virus (TBE complex) |
| Pestivirus | M31182 | DNA equivalent of the genome of the BVD virus |
| Pestivirus | M31768 | DNA equivalent of the genome of the Brescia strain of the CSF virus (hog cholera virus) |
| Pestivirus | J04358 | DNA equivalent of the genome of the Alfort strain of the CSF virus (hog cholera virus) |
| Hepacivirus | M62321 | cDNA of the polyprotein of the hepatitis C virus type 1 (HCV-1) |
| Hepacivirus | D90208 | cDNA of the polyprotein of the hepatitis C virus |
| Hepacivirus | M58335 | Complete cDNA of the polyprotein of the hepatitis C virus |

The positions of the coding sequences of the various Flaviviridae proteins are indicated in the sequences corresponding to the accession numbers listed in Table 1, which correspond to the cDNAs of the polyprotein or to the DNA equivalents of the Flaviviridae genome.

According to yet another advantageous embodiment of said use, said polynucleotide fragment is selected from:

a) the cDNAs encoding an E protein and, optionally, a prM or M protein, and/or a C protein, and/or a non-structural protein of West Nile virus or of dengue virus, and the cDNAs encoding one or more immunogenic peptides of at least 8 amino acids of the above proteins, b) the cDNAs encoding an E1 or E2 protein or an E1/E2 heterodimer, and/or a C protein according to a 0, +1 or +2 reading frame, and/or an NS3 protein of hepatitis C virus, and the cDNAs encoding one or more immunogenic peptides of at least 8 amino acids of the above proteins, and c) the cDNAs encoding one or more different domains III (positions 295 to 394) of an E protein of dengue virus, each corresponding to one of the four types of dengue virus (types 1 to 4 or DEN-1 to DEN-4), preferably a cDNA encoding the four domains III (DEN-1 to DEN-4), the sequences of which are represented by SEQ ID NOs. 1-4 in the sequence listing attached in the appendix.

According to an advantageous provision of said use, said cDNA encoding a C protein according to a +1 or +2 reading frame is selected from the group consisting of the sequences SEQ ID NOs. 5 to 14.

In accordance with the invention, said membrane proteins (prM or M) and/or envelope proteins (E, E1, E2) are expressed by the recombinant lentiviral vector as defined above, either in membrane form, located in the plasma membrane, at the surface of the cells, or in secreted form, i.e. exported from the cell, to the extracellular medium.

In addition, when the Flavivirus prM and E proteins are expressed simultaneously in the cells transduced by the recombinant vector (in vitro or in vivo), they assemble as viral pseudoparticles (or virus-like particles, VLPs) that are secreted into the extracellular medium. Such particles are particularly immunogenic and induce the production of neutralizing antibodies.

The cDNA encoding said membrane form comprises the sequence encoding the mature protein, preceded by a sequence encoding a signal peptide for translocation in the endoplasmic reticulum, which sequence includes a translation initiation codon (ATG) at its 5' end. In the case of the Flaviviruses, said signal sequence is advantageously derived from the M protein precursor (prM). The cDNA encoding said secreted form comprises the sequence encoding a truncated mature protein, from which the membrane anchoring region has been deleted and which is preceded by a signal peptide as defined above.

For example, in the case of the West Nile virus:
the mature E protein corresponds to positions 291 to 791 of the polyprotein sequence, with reference to the Genbank sequence AAL87234; the corresponding nucleotide sequence is located from positions 967 to 2469 in the sequence of the genome of the West Nile virus, with reference to the Genbank sequence AF481864;
a truncated mature E protein from which the membrane anchoring region has been deleted corresponds in particular to positions 291 to 732 of the sequence of the polyprotein of the West Nile virus, with reference to the Genbank sequence AAL87234; the corresponding nucleotide sequence is located from positions 967 to 2292 in the sequence of the genome of the West Nile virus, with reference to the Genbank sequence AF481864;
the internal signal peptide derived from the M protein precursor corresponds to positions 275 to 290 of the sequence of the polyprotein, with reference to the Genbank sequence AAL87234; the corresponding nucleotide sequence is located from positions 919 to 966 in the sequence of the genome of West Nile virus, with reference to the Genbank sequence AF481864.

Thus, the cDNAs encoding the membrane form of the E protein, the secreted form of the E protein and the prM and E proteins of the West Nile virus correspond, respectively, to positions 919 to 2469, 919 to 2292 and 399 to 2469 in the sequence of the genome of said virus as defined above.

A subject of the present invention is also a recombinant lentiviral vector comprising a polynucleotide fragment encoding at least one structural protein of a Flaviviridae or an immunogenic peptide of at least 8 amino acids of said protein; in addition, as specified above in the context of the use of such vectors, said vector advantageously also comprises a cDNA encoding one or more non-structural proteins and/or one or more immunogenic fragments of said proteins. Said polynucleotide fragment is in particular selected from the sequences as defined above. Advantageously, said recombinant lentiviral vector is a vector of triplex type. In addition, said recombinant lentiviral vector can advantageously comprise a 3' LTR in which the promoter and the activator has been deleted from the U3 region. It is preferably a vector that is pseudotyped with at least one envelope protein of another virus, preferably the vesicular stomatitis virus (VSV) glycoprotein G.

According to an advantageous embodiment of said vector, it comprises the cDNA encoding at least one E protein and, optionally, a prM or M protein, and/or a C protein, and/or a non-structural protein of West Nile virus or of dengue virus, or the cDNA encoding one or more immunogenic peptides of at least 8 amino acids of the above proteins.

According to another advantageous embodiment of said vector, it comprises the cDNA encoding an E1 or E2 protein or an E1/E2 heterodimer, and/or a C protein according to a 0, +1 or +2 reading frame and, optionally, an NS3 protein of hepatitis C virus, or the cDNA encoding one or more immunogenic peptides of at least 8 amino acids of the above proteins.

According to an advantageous provision of said vector, said cDNA encoding a C protein according to a +1 or +2 reading frame is selected from the group consisting of the sequences SEQ ID NOs. 5 to 14.

According to yet another advantageous embodiment of said vector, it comprises the cDNA encoding a domain III (positions 295 to 394) or several different domains III of an E protein of dengue virus, each corresponding to one of the four types of dengue virus (types 1 to 4 or DEN-1 to DEN-4), preferably it comprises a cDNA encoding the four domains III (DEN-1 to DEN-4) the sequences of which are represented by SEQ ID NOs. 1-4 in the sequence listing attached in the appendix.

According to yet another advantageous embodiment of said vector, it is a vector plasmid called pTRIPΔU3.CMV-sE (WNV), comprising the cDNA encoding a secreted form of the E protein of the IS-98-ST1 strain of West Nile virus, which vector is included in a microorganism deposited under the No. I-3076, on 27 Aug. 2003, with the Collection Nationale de Cultures de Microorganismes [National Collection of Cultures of Microorganisms], 25 rue du Docteur Roux, 75724 Paris Cedex 15.

The invention encompasses the vector plasmids as defined above and the vector particles derived from the above vector particles, in particular the vector particles pseudotyped with at least one envelope protein of another virus, such as in particular the vesicular stomatitis virus (VSV) glycoprotein G.

The recombinant lentiviral vectors as defined above are prepared by conventional methods, that are known in themselves, and according to standard protocols such as those described in *Current Protocols in Molecular Biology* (Frederick M. AUSUBEL, 2000, Wiley and son Inc., Library of Congress, USA).

More precisely, the polynucleotide fragments can be obtained either by amplification of a matrix consisting of a genomic RNA or an mRNA of a Flaviviridae or else a cDNA or a DNA fragment derived from the above, by PCR or RT-PCR using primers specific for the genome of a virus of the family Flaviviridae, or by digestion of the Flaviviridae cDNA using a restriction enzyme, or alternatively by total or partial chemical synthesis.

The polynucleotide fragment thus obtained is cloned into a vector plasmid containing the lentiviral vector genome, so as to produce a recombinant vector plasmid.

The particles of the recombinant lentiviral vector (vector particles) are produced by cotransfection of cells with the recombinant vector plasmid as defined above, an encapsidation plasmid that provides, in trans, the structural proteins and the enzymes of the viral particle and, optionally, a plasmid for expression of the envelope glycoprotein of a virus such as VSV, for the production of pseudotyped particles.

A subject of the present invention is also an immunogenic composition, characterized in that it comprises at least one recombinant vector as defined above.

According to an advantageous embodiment of said composition, it comprises a pharmaceutically acceptable vehicle and, optionally, a carrier substance.

The pharmaceutically acceptable vehicles and the carrier substances are those conventionally used.

The carrier substances are advantageously selected from the group consisting of unilamellar liposomes, multilamellar liposomes, saponin micelles or solid microspheres of a saccharide or auriferous nature.

According to another advantageous embodiment of said composition, it comprises particles of said recombinant lentiviral vector (vector particles), preferably pseudotyped with an envelope protein of another virus, preferably with the vesicular stomatitis virus glycoprotein G.

According to yet another advantageous embodiment of said composition, it comprises a recombinant lentiviral vector of triplex type as defined above.

According to an advantageous provision of said composition, it comprises an isolated nucleic acid molecule corresponding to the recombinant genome of said recombinant lentiviral vector of triplex type, which nucleic acid molecule comprises: (i) the regulatory sequences for encapsidation, reverse transcription and integration and the cis-active sequences for central initiation (or polypurine tract cPPT) and termination (CTS) of lentiviral origin and, optionally, the regulatory sequences for the Rev protein (RRE or Rev Responsive Element) and (ii) a polynucleotide fragment encoding a Flaviviridae protein or an immunogenic peptide of at least 8 amino acids of said protein as defined above.

In accordance with the invention, said vector of triplex type comprises an expression cassette that includes the suitable regulatory elements for transcription (promoter, enhancer, Kozak consensus sequence, polyadenylation signal, etc.) under the control of which are inserted the coding sequences as defined above, and said coding sequences of interest optionally comprise the signals required for cellular transport, as defined above.

The immunogenic or vaccine compositions according to the invention can be administered generally (orally, intramuscularly, subcutaneously, intraperitonealy or intravenously), locally (nasally, other mucosal routes) or by a combination of these routes, in a sensitive species as defined above (human or non-human mammalian host, or reservoir (birds, reptiles)).

Preferably, they are administered subcutaneously in order to target antigen-presenting cells such as dendritic cells, so as to obtain prolonged expression of the antigen in these cells.

Alternatively, the immunogenic or vaccine compositions according to the invention are used to modify autologous cells of a host species, in particular antigen-presenting cells such as dendritic cells. The modified cells are then re-administered to the host; such a use is particularly advantageous for the treatment of an infection with a Flaviviridae in a human or non-human host mammal.

The dose of vector varies according to the route of administration, and also according to the nature and the weight of the species to be treated (human or animal).

A subject of the present invention is also cells modified with a recombinant vector as defined above. Preferably, said cells are eukaryotic cells that are stably modified with said recombinant vector; such cells that stably express at least one protein or one antigenic peptide of Flaviviridae are useful:
 for producing particles of said recombinant lentiviral vector (vector particles),
 for producing recombinant viral proteins of Flaviviridae, immunogenic fragments of said proteins, and viral pseudoparticles of the type of those of Flaviviridae (VLPs or virus-like particles), derived from the envelope proteins and/or membrane proteins of Flaviviridae, in particular from the Flavivirus prM and E proteins; the pseudoparticles are advantageously used as a reagent for diagnosing a Flaviviridae infection by immunocapture of the specific immunoglobulins present in the biological fluids of infected individuals,
 for screening antiviral compounds, and
 as a diagnostic reagent.

In accordance with the invention, it is possible to produce viral proteins of Flaviviridae and/or immunogenic fragments of said proteins or else viral pseudoparticles, in accordance with the following steps:
 a) culturing modified cells as defined above, under conditions which allow the expression of one or more viral proteins of Flaviviridae and/or one or more of the immunogenic fragments of said proteins encoded by said recombinant lentiviral vector, and
 b) separating said proteins, protein fragments or pseudoparticles from the culture supernatant or from said cells in a), by any suitable means.

In accordance with this method, the purification of viral protein(s) or of fragment(s) can be carried out, from a culture supernatant, or from lysates of the cells modified with a recombinant vector as defined above, by conventional techniques such as:
 affinity chromatography: a tag, such as a nucleotide sequence encoding a polyhistidine tail is then introduced into the vector, and the protein is purified on nickel-gel (agarose or the like) columns;
 immunoaffinity chromatography: the viral sequence of interest is fused, at the C-terminal or at the N-terminal, with a nucleotide sequence encoding a peptide epitope, also comprising a site for cleavage by an enzyme, such as thrombin, in order to subsequently separate the epitope sequence from the protein; useful epitopes are, for example, the C9 epitope (TETSQVAPA) (Mirzabekov T. et al., J. Biol. Chem., 1999, 274, 28745-28750)

or the myc epitope. The expressed protein is purified on an affinity column to which an antibody specific for said epitope has been attached (1D14 for the C9 epitope or $9^E10$ for the myc epitope) and the protein of interest is separated by means of cleavage with thrombin;

precipitation with a precipitating agent such as polyethylene glycol, and then centrifugation in order to recover the protein in the pellet.

In accordance with this method, the purification of the particles of the type of those of Flaviviridae is carried out, from a culture supernatant from cells modified with a recombinant vector as defined above, by conventional techniques such as:

precipitation with a precipitating agent such as polyethylene glycol, and then centrifugation in order to recover the pseudoparticles in the pellet, and continuous or discontinuous gradient centrifugation, in particular on a sucrose gradient.

A subject of the present invention is also a method for screening antiviral compounds, characterized in that it comprises:

bringing eukaryotic cells modified with a recombinant vector as defined above, and in particular with a vector comprising a cDNA encoding a non-structural protein of Flaviviridae such as NS3 (helicase or protease) or NS5 (polymerase), into contact with various compounds of a library to be tested, and measuring, by any suitable means, the activity (helicase, protease, polymerase) of said protein, in the presence or in the absence of said compounds, and selecting the compounds capable of modulating (activating or inhibiting) said activity.

This activity is evaluated by conventional methods known to those skilled in the art, such as those described in particular in Borowski et al., Acta Biochimica Polonica, 2002, 49, 597-614; Steffens et al., J. Gen. Virol., 1999, 80, 2583-2590; Ryan et al., J. Gen. Virol., 1998, 79, 947-959; Bretner et al., Antivir. Chem. Chemother., 2004, 15, 35-42.

Preferably, the screenings are carried out on specific target tissues, and in particular on dendritic cells, neuronal cells or hepatocytes.

A subject of the present invention is also a method for diagnosing infection with a Flaviviridae, using a sample of biological fluid from an individual of a sensitive species, characterized in that it comprises at least the following steps:

a) bringing said biological sample into contact with modified eukaryotic cells expressing at least one Flaviviridae antigen (C, E, E1, E2, prM, M, NS (in particular NS1)) as defined above, optionally permeabilized, b) revealing, by any suitable means, the antigen-antibody complexes formed in (a), for example by EIA, ELISA or RIA, or by immunofluorescence.

A subject of the present invention is also a method for diagnosing infection with a Flaviviridae using a sample of biological fluid from an individual of a sensitive species, characterized in that it comprises at least the following steps:

a) bringing said biological sample into contact with viral pseudoparticles produced from the culture supernatant of cells modified with a lentiviral vector expressing at least one membrane protein and/or envelope protein as defined above, and b) revealing, by any suitable means, the antigen-antibody complexes formed in (a), for example by EIA, ELISA or RIA, or by immunofluorescence.

A subject of the present invention is also a kit for carrying out the methods as defined above, characterized in that it comprises at least modified cells as defined above.

A subject of the present invention is also a method of immunization against a Flaviviridae, characterized in that it comprises a single administration of a recombinant vector as defined above, preferably subcutaneously.

Besides the above provisions, the invention also comprises other provisions, which will emerge from the following description that refers to examples of preparation of the recombinant vector according to the present invention and of use of said vector for immunization, and derived modified cells for the production of proteins, and also to the attached drawings in which:

FIG. 2 illustrates the analysis by ELISA and by means of a neutralization assay, of the sera from mice immunized with a single intraperitoneal injection of 1 μg of TRIPΔU3CMV-sE (WNV) vector particles.

Figure 1:
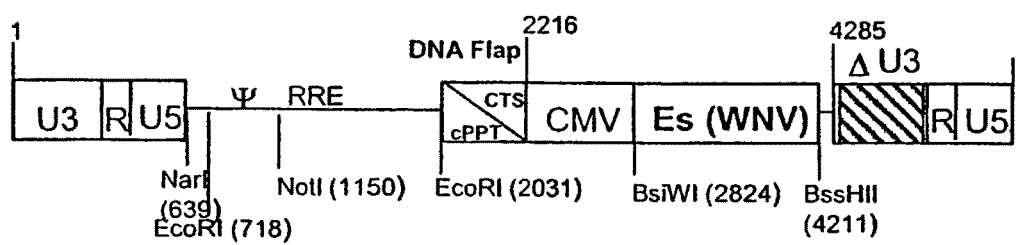
FIG. 1 is a diagrammatic representation of the vector plasmid pTRIPΔU3CMV-sE(WNV) corresponding to the sequence SEQ ID NO. 15, containing the cDNA (SEQ ID NO. 16) encoding the truncated E protein (E 1-411) of the West Nile virus (SEQ ID NO. 17).

Lanes 1 to 10: lysates of VERO cells infected with West Nile virus were precipitated with the following sera:
lane 1: serum at D14 post-immunization with the TRIPΔU3CMV-GFP vector,
lane 2: serum at D23 post-immunization with the TRIPΔU3CMV-GFP vector,
lane 3: polyclonal anti-West Nile virus (strain IS-98-ST1) ascites,
lane 4: non-immune serum,
lane 5: serum at D14 post-immunization with the TRIPΔU3CMV-sE(WNV) vector,
lane 6: serum at D23 post-immunization with the TRIPΔU3CMV-sE(WNV) vector,
lane 7: serum at D22 post-challenge (10 $LD_{50}$ of the IS-98-ST1 strain) from the mice immunized for 14 days with the TRIPΔU3CMV-sE(WNV) vector,
lane 8: serum at D30 post-challenge (10 $LD_{50}$ of the IS-98-ST1 strain) from the mice immunized for 14 days with the TRIPΔU3CMV-sE(WNV) vector,
lane 9: serum at D22 post-challenge (100 $LD_{50}$ of the IS-98-ST1 strain) from the mice immunized for 30 days with the TRIPΔU3CMV-sE(WNV) vector,
lane 10: serum from mice immunized with the lymphocytic choriomeningitis virus.

Lanes 11 and 12: lysates of non-infected VERO cells were precipitated with the following sera:
lane 11: polyclonal anti-West Nile virus (IS-98-ST1 strain) ascites,
lane 12: serum at D22 post-challenge (100 $LD_{50}$ of the IS-98-ST1 strain) from the mice immunized for 30 days with the TRIPΔU3CMV-sE(WNV) vector.

Figure 4:
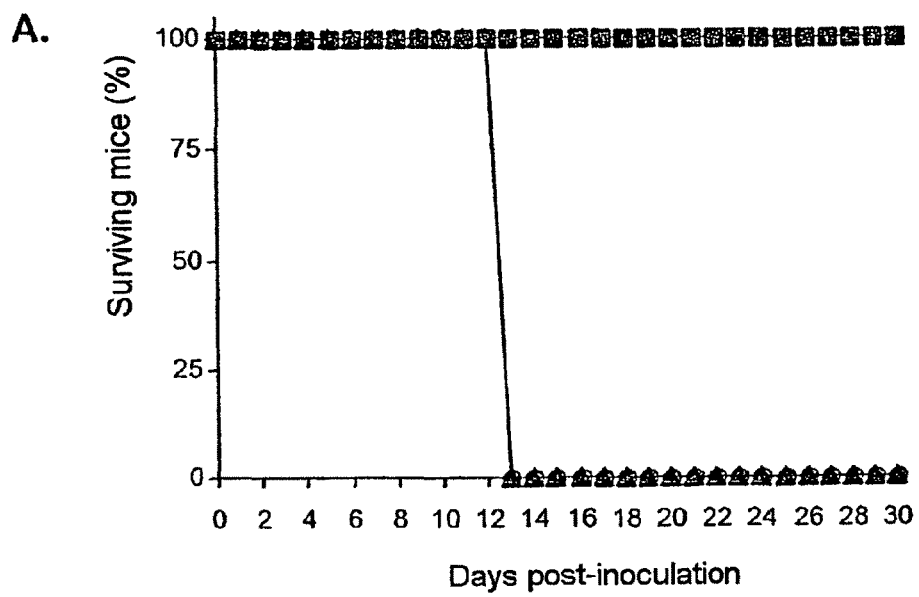
Figure 4:
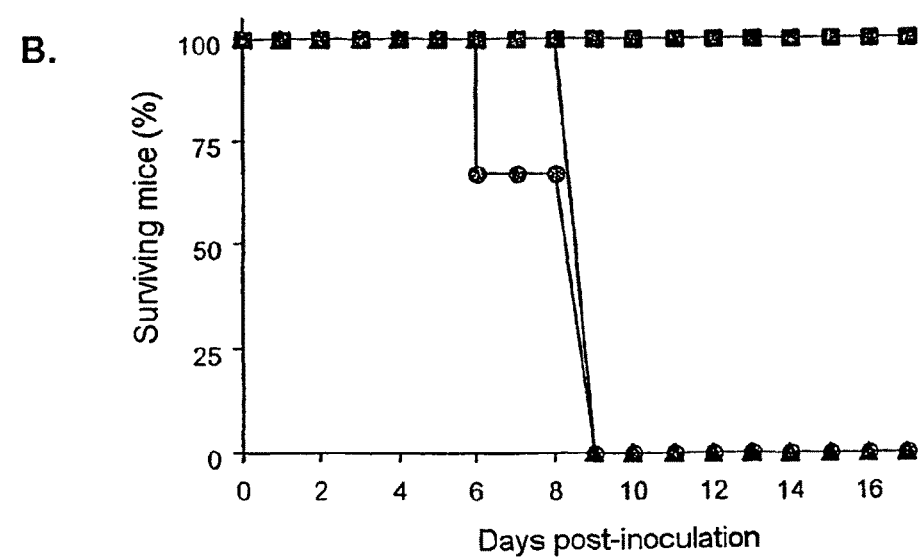

FIG. 4 represents the survival curve for the mice immunized intraperitoneally and then challenged by the same route, either 2 weeks after immunization, with 10 $LD_{50}$ of the IS-98-ST1 strain (A), or 4 weeks after immunization, with 100 $LD_{50}$ of the IS-98-ST1 strain (B). ●: control mice inoculated with DPBS. ▲: control mice immunized with 1 μg of TRIPΔU3CMV-EGFP vector particles. ■: mice immunized with 1 μg of TRIPΔU3CMV-sE(WNV) vector particles.

Figure 5:
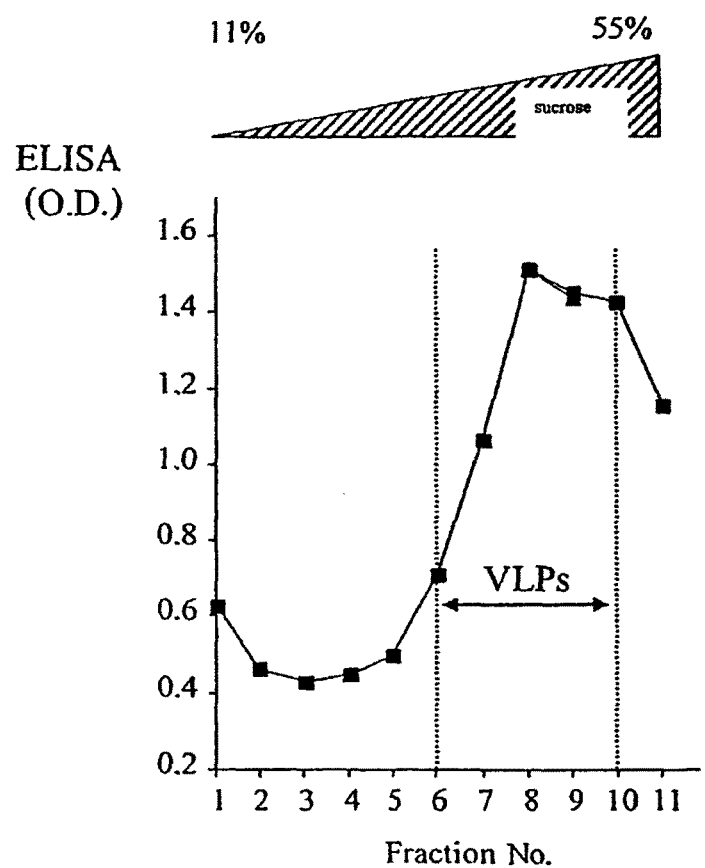

FIG. 5 illustrates the purification of viral pseudoparticles from the supernatant of eukaryotic cells transduced with a recombinant lentiviral vector expressing the prM and E proteins of the West Nile virus.

FIG. 6 illustrates the detection of anti-WNV-sE antibodies in sera from TRIPΔU3.CMV-sE(WNV) vaccinated 129 mice. Radio-labeled cell lysates from WNV infected Vero cells were immunoprecipitated with pooled immune sera from lentiviral vector vaccinated 129 mice. (A) Pre-WNV challenge sera. (B) Post-challenge sera. HMAF=Hyperimmune Mouse Ascitic Fluid. Control sera=non immune sera. Antisera to MV=antisera to Measle Virus. TRIP/WNsE=TRIPΔU3.CMVsE(WNV). TRIP/GFP=TRIPΔU3.CMV-GFP.

Figure 7:
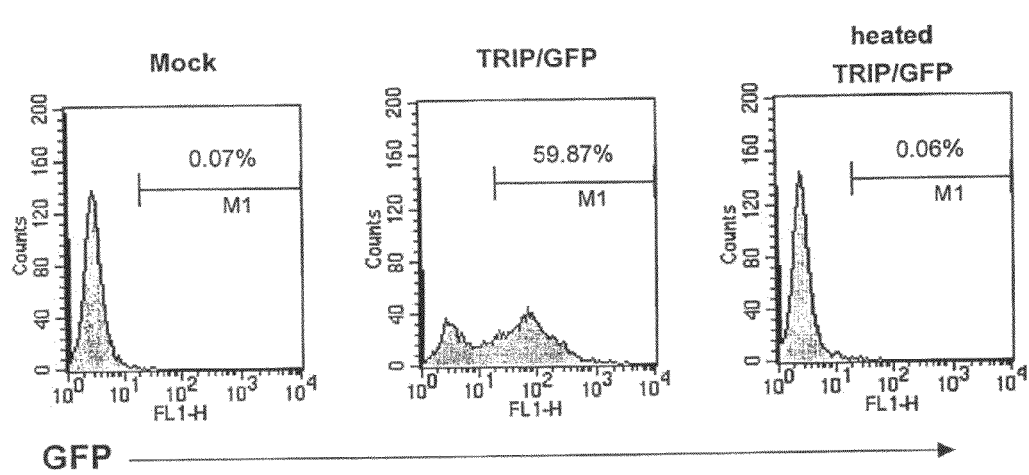

FIG. 7 illustrates the analysis by flow cytometry of the effect of heat treatment on recombinant lentiviral vector transduction efficiency. 293T cells were incubated with TRIPΔU3.CMV-GFP vector particles which have been heat-inactivated for 10 min at 70° C. (heated TRIP/GFP), or not inactivated (TRIP/GFP). Non-infected 293T cells (Mock) were used as control. At 48 h, the GFP fluorescence intensity was measured; the percentage of GFP positive cells is indicated.

EXAMPLE 1

Preparation of the TRIPΔU3.CMV-sE(WNV) Recombinant Vector

1) Construction of the pTRIPΔU3.CMV-sE(WNV) Vector Plasmid

A cDNA representing the nucleotide sequence from positions 967 to 2292 of the genome of the IS-98-ST1 strain of the West Nile virus (application FR 01 04599 and Genbank AF481864), corresponding to the amino acids from positions 291 to 732 of the polyprotein (application FR 01 04599 and Genbank AAL87234), was amplified by polymerase chain reaction (PCR) using the sense primer: 5'-TAT CGTACGATGAGAGTTGTGTTTGTCGTGCTA-3' (SEQ ID NO. 18), containing the BsiW I site in the underlined form) and the antisense primer: 5'-ATA GCGCGCTTAGACAGCCCTTCCCAACTGA-3' (SEQ ID NO. 19), containing the BssH II site in the underlined form. This cDNA, corresponding to the sequence SEQ ID NO. 16 in the sequence listing attached in the appendix, is bordered, in the 5' position, by a BsiW I site and, in the 3' position, by a BssH II site. The sequence SEQ ID NO. 16 contains, successively from 5' to 3': an ATG, the sequence encoding the signal peptide derived from the M protein precursor (prM 151-166) and the sequence encoding a truncated E protein (E 1-441), from which the membrane anchoring region has been deleted. It encodes an E protein which is secreted into the extracellular medium (sE protein); the signal peptide derived from the prM protein is used for translocation of the E protein in the endoplasmic reticulum and for its transport, in secretion vesicles, to the plasma membrane, where it is released into the extracellular medium.

The lentiviral vector plasmid pTRIPΔU3.CMV-EGFP (application WO 01/27302) was digested so as to excise the EGFP gene, and then the linearized plasmid was ligated with a linker containing the BsiW I and BssH II sites, so as to give the plasmid called pTRIPΔU3.CMV-BsiW I-BssH II. The 1.4 kb BsiW I-BssH II fragment of the cDNA obtained above, that includes the sE protein construct, was cloned into the same sites of the plasmid pTRIPΔU3.CMV-BsiW I-BssH II, to give the recombinant lentiviral vector plasmid called pTRIPΔ3.CMV-sE (WNV) or pTRIPΔU3.CMV-sE (WNV) (FIG. 1 and SEQ ID NO. 15). A culture of E. coli bacteria transformed with the pTRIPΔU3.CMV-sE (WNV) vector plasmid was deposited, under the No. I-3076, on 27 Aug. 2003, with the Collection Nationale de Cultures de Microorganismes [National Collection of Cultures of Microorganisms], 25 rue du Docteur Roux, 75724 Paris Cedex 15.

The conformity of the pTRIPΔU3.CMV-sE (WNV) recombinant vector plasmid was verified by enzyme restriction and by sequencing of the insert corresponding to the sE protein construct.

The sequence of the 1.4 kb BsiW I-BssH II insert corresponds to the nucleotide sequence SEQ ID NO. 16 in the sequence listing attached in the appendix; it encodes a secreted E protein, called sE, corresponding to the amino acid sequence SEQ ID NO. 17 in the sequence listing attached in the appendix.

2) Preparation of Viral Particles of the TRIPΔU3.CMV-sE (WNV) Vector, Pseudotyped with the Vesicular Stomatitis Virus Envelope Glycoprotein (VSV-G)

Human fibroblastic 293T cells (ATCC) are grown in Dulbecco's modified Eagle medium (DMEM) Glutamax (GIBCO) supplemented with 10% Fetal Calf Serum (FCS). The viral particles of the TRIPΔU3.CMV-sE (WNV) vector, pseudotyped with the vesicular stomatitis virus envelope glycoprotein (VSV-G), also called TRIPΔU3.CMV-sE (WNV) vector particles, are produced by calcium phosphate cotransfection of the 293T cell line with the pTRIPΔU3.CMV-sE (WNV) vector plasmid as defined above, an encapsidation plasmid that provides, in trans, the structural proteins and the enzymes of the viral particle (pCMVAR8.2: Naldini et al., Science, 1996, 272, 263-267; pCMVΔR8.91 or p8.7: Zufferey et al., Nat. Biotechnol., 1997, 15, 871-877) and a plasmid for expression of the VSV virus envelope glycoprotein (pHCMV-G: Yee et al., P.N.A.S., 1994, 91, 9564-9568), as described in Zennou et al., Cell., 2000, 101, 173-185).

3) Expression of the Secreted Version of the E Glycoprotein of WNV (WNV-sE) by the Recombinant TRIPΔU3.CMV-sE (WNV) Vector Expression of WNV-sE in lentiviral vector transduced 293T cells was examined by indirect immunofluorescence. Briefly, human 293T cells cultured on 8-chamber Glass-Labteks (NUNC) were transduced with TRIPΔU3.CMV-sE (WNV) vector. After 48 h, cells were fixed with 3% paraformaldehyde (PFA) in PBS for 20 min and permeabilized with 0.1% Triton X-100 in PBS for 4 min. Cells were incubated with anti-WNV HMAF at a 1:100 diluton in PBS for 1 h. After blocking with 0.2% BSA in PBS, cells were further incubated with a Cy3-conjugated anti-mouse IgG antibody (AMERSHAM PHARMACIA) at a 1:500 dilution in PBS 0.2% BSA. Cell nuclei were visualized with DAPI. The slides were examined using a Zeiss Axioplan microscope with ApoTome system.

At 48 h post-transduction, a high fraction of cells were immunostained. Immunostaining pattern suggests that WNV-sE migrated through the secretory pathway.

4) Titration of the Recombinant TRIPΔU3.CMV-sE (WNV) Vector 4.1) Material and Methods a) p24 Antigen Titration by ELISA Quantification of p24 antigen content of concentrated vector particles was done with a commercial HIV-1 p24 ELISA kit (PERKIN ELMER LIFESCIENCES).

b) Quantitative PCR

Primers and probes were synthesized by PROLIGO. For detection of the U5-R sequences in the lentiviral vector, primers and probes used (Brussel A and Sonigo P, J. Virol., 2003, 77, 10119-10124), were as follows (SEQ ID NO: 20 to 27):

probes (3' fluorescein (PITC) or phosphorylated (P))

```
LTR-FL:     5'-CACAACAGACGGGCACACACTACTTGA-FITC-3'

LTR-LC:     5'-RED640-CACTCAAGGCAAGCTTTATTGAGGC-P-3'
``` primers

```
AA55M:      5'-GCTAGAGATTTTCCACACTGACTAA-3'

M667:       5'-GGCTAACTAGGGAACCCACTG-3'.
```

For detection of CD3, the sequences of primers and probes were as follows:
probes

```
CD3-P1:     5'-GGCTGAAGGTTAGGGATACCAATATTCCTGTCTC-
            FITC-3',

CD3-P2:     5'RED705-CTAGTGATGGGCTCTTCCCTTGAGCCCTTC-
            P-3'
``` primers

```
CD3-in-F:       5'-GGCTATCATTCTTCTTCAAGGTA-3'

CD3-in-R:       5'-CCTCTCTTCAGCCATTTAAGTA-3'.
```

Genomic DNA from approximately $3.10^6$ lentiviral vector transduced 293T cells was isolated 48 h after transduction using QIAamp® DNA Blood Mini Kit (QIAGEN). For real-time PCR analysis, 5 μL of DNA were mixed with 15 μL of a PCR master mix consisting of 1× Jumpstart™ Taq Ready-Mix™ (SIGMA), 1.9 mM $MgCl_2$, 1.5 μM of forward and reverse primers (AA55M/M667 or CD3-in-F/CD3-in-R), 200 nM of the probes (LTR-FL/LTR-LC or CD3-P1/CD3-P2) and, 1.5 units of Taq DNA Polymerase (Invitrogen). Amplifications were performed using one cycle of 95° C. for 3 min, and 40 cycles of 95° C. for 5 s, 55° C. for 15 s and 72° C. for 10 s. To take into account the possible plasmid contamination of vector stocks, DNA from 293T cells transduced with heat-inactivated (10 min at 70° C.) vector was always tested in parallel. For negative controls 5 μL of genomic DNA from untransduced cells was used. Each DNA sample was tested in duplicate and the mean values are reported. Ten-fold serial dilutions of known concentration of the plasmid pTripCD3, containing the relevant sequences U5-R and CD3, were amplified in parallel with DNA samples to generate a standard curve.

The total number of vector copies per cell was calculated by normalizing the number of U5-R copies to the number of 293T cells, as quantified by the copy number of CD3 molecules on the same genomic DNA sample, and then subtracting the number of copies obtained for the heat-inactivated vector-transduced cells.

4.2) Results

The number of physical particles of the vector stock used in this study was first evaluated using a commercially available ELISA assay against the p24 HIV-1 capsid protein. The determined concentration was 58 ng of p24 per microliter.

The vector stock actual titer was calculated on the basis of the transfer of vector DNA to the target cell, using a quantitative PCR assay. The quantification of both a vector specific sequence (U5) and a cellular locus (CD3) gives the average DNA vector copy number per cell. This allows the calculation, after transduction with a defined concentration of vector particles, of the titer of the vector preparation. The TRIPΔU3.CMV-sE vector stock used in this study was titrated in human 293T cells at $5.2 \times 10^7$ transduction units (TU) per ml. In other words, 1 ng of p24 antigen from this TRIPΔU3.CMV-sE vector preparation can transduce 900 human 293T cells.

For simplicity reasons, in the following sections, the quantity of vector particles used will be expressed as ng of p24 antigen.

EXAMPLE 2

Analysis of the Immunogenic Capacity of the TRIPΔU3.CMV-sE Vector in BALB/c Mice 1) Materials and Methods 1.1) Immunization/Vaccination Protocol Six-week-old BALB/c mice (2 groups of 6 mice; Janvier breeding colony) were inoculated intraperitoneally with 0.1 ml of Dulbecco's PBS (DPBS) containing 1 μg of TRIPΔU3.CMV-sE vector particles prepared as described in Example 1. The animals were given a single vaccine injection.

The control groups were inoculated, under the same conditions, either with 1 μg of TRIPΔU3.CMV-GFP vector particles prepared in a similar manner to the TRIPΔU3.CMV-sE (WNV) vector particles (2 groups of 3 mice), or DPBS buffer alone (2 groups of 3 mice).

The mouse sera were taken 14 days ($D_{14}$) and 23 days ($D_{23}$) after the vaccine injection and heat-inactivated for 30 min at 56° C. before measurement of the antibody response.

1.2) West Nile Virus Strain, Purification and Titering

The West Nile virus strain used is the IS-98-ST1 strain, described in application FR 01 04599; it is produced on *Aedes* mosquito cells (AP61 line) and purified according to the protocol described by Després et al., Virol., 1993, 196, 209-219. More precisely, AP61 cells are infected, at a multiplicity of infection of 0.4, with the IS-98-ST1 strain of the West Nile virus. Three days after infection, the viral particles present in the culture supernatant are precipitated with PEG 6000 (7%), and then purified on a discontinuous 30-60% sucrose gradient and on a linear 10-50% sucrose gradient. The virions thus obtained are conserved at −80° C. in sucrose (30%).

The West Nile virus is titered by means of a Focus ImmunoAssay (FIA) on AP61 cells, and the infectious titre is expressed as focus-forming units ($FFU_{AP61}$/ml), according to the protocol described by Després et al., mentioned above.

The infectious titres of the purified viral preparations are approximately $10^{10}$ $FFU_{AP61}$/ml.

1.3) Anti-WNV Hyperimmune Ascitic Fluid

Anti-WNV hyperimmune mouse ascitic fluid (HMAF) was obtained by repeated immunization of adult mice with WNV strain IS-98-ST1, followed by the inoculation of sarcoma 180. Mouse polyclonal anti-WNV antibodies were obtained by immunization of adult WNV-resistant BALB/c-MBT congenic mice with $10^3$ FFU of IS-98-ST1 as described previously (Mashimo et al., PNAS, 2002, 99, 11311-11316). The WNV-immune serum was collected one month after priming.

1.4) ELISA

The anti-E total antibodies titres are measured by ELISA according to the protocol described in Mashimo et al., PNAS, 2002, 99, 11311-11316, using, as antigen, WN IS-98-ST1 virions purified on a sucrose gradient as described in paragraph 1.2 ($10^6$ $FFU_{AP61}$ per 96-well microplate). Peroxidase-conjugated anti-mouse immunoglobulin (H+L) (JACKSON IMMUNO RESEARCH) at a 1:4000 dilution, peroxidase-conugated anti-mouse IgM (μ-chain specific) (SIGMA) at a 1:20,000 or peroxidase-conjugated anti-mouse IgG (γ-chain specific) (Sigma) at a 1:20,000 dilution were used as secondary antibodies. The titres are determined by means of the final dilution of serum that corresponds to the optical density (OD) value which is at least twice that of the serum from the control animals, as defined above. The anti-E IgG and IgM antibodies are also measured using an already described isotype specific ELISA (Despres P et al., J. Infect. Dis., 2005, 191, 207-214).

1.5) Immunoprecipitation (RIP Assay)

The experimental protocol is as described in Després et al. (J. Virol., 1995, 69, 7345-7348). More precisely, VERO cells are infected with the IS-98-ST1 strain of the West Nile virus, at the multiplicity of infection of 5 $FFU_{AP61}$/cell. Twenty hours after infection, the cell proteins are labelled with Tran$^{35}$Slabel (ICN; 100 µCi/ml) for 3 hours. After three washes with cold PBS, cells are lysed in RIPA buffer (50 mM Tris-Cl, pH 8.0, 150 mM NaCl, 10 mM EDTA, 0.1% SDS, 0.5% sodium deoxycholate, 1% Triton X-100, supplemented with 25 µg/ml aprotinin (SIGMA) for 10 min at +4° C. The cell lysates are then clarified by centrifugation at 10,000 rpm for 5 min at +4° C. The lysates are incubated with the sera to be tested at the final dilution of 1:100, in the presence of Protein A Sepharose. The immunoprecipitates are then analysed in an SDS-15% PAGE gel, under non-reducing conditions, and revealed by autoradiography.

1.6) Neutralization Test

The neutralizing activity of the sera from the immunized mice, with respect to the IS-98-ST1 strain of the West Nile virus, was measured by the reduction in viral replication foci on VERO cells (ATCC). More precisely, serial dilutions of the sera inactivated for 30 minutes at 56° C. (0.1 ml) are incubated in the presence of an inoculum of the IS-98-ST1 strain of the West Nile virus (100 $FFU_{AP61}$ in 0.1 ml). VERO cells ($1.5 \times 10^5$ cells per well of a 12-well plate) are then infected with the mixture for two hours at 37° C., and the viral replication foci are counted two days after infection. The neutralizing antibody titre of the sera, called TNRF90 (Test for Neutralization by 90% Reduction in viral replication Foci), is determined by virtue of the final dilution of the serum that neutralizes at least 90 of the 100 FFUs of viruses inoculated in each well.

2) Results 2.1) Analysis by ELISA of the Reactivity of the Sera from the Immunized Animals, with Respect to West Nile Virus The production of antibodies directed against the E protein of West Nile virus was verified by ELISA assay carried out of the mouse sera taken 14 and 23 days after the injection of TRIPΔU3.CMV-sE (WNV) vector particles, using purified West Nile virus as antigen.

The results given in FIG. 2 show that the specific antibody titre of the sera from the mice immunized with the TRIPΔU3.CMV-sE (WNV) vector particles is 1/10 000 and 1/20 000, respectively, 14 days and 23 days after the vaccine injection.

Figure 3:
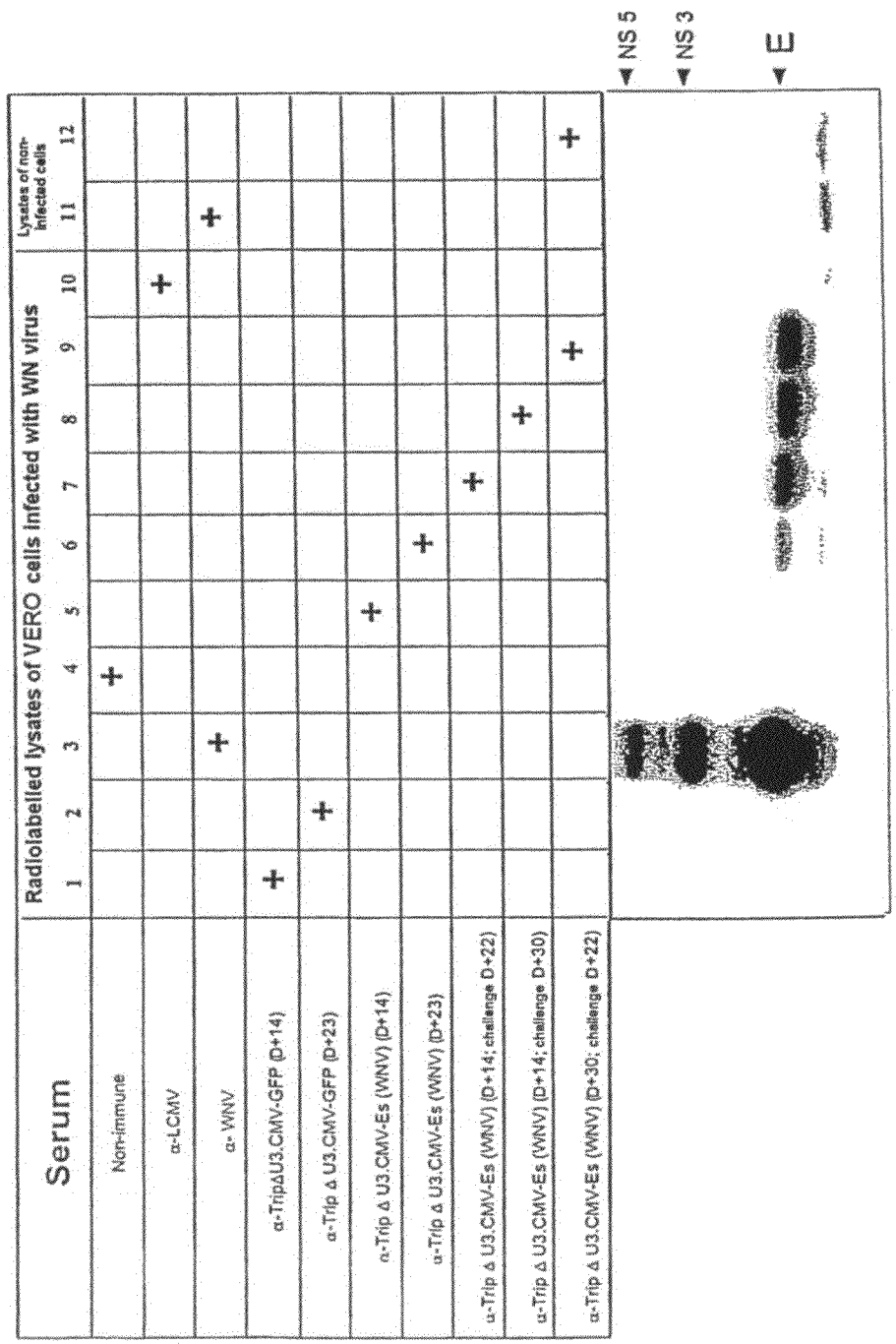
FIG. 3 represents the immunoprecipitation of the lysates of VERO cells infected with West Nile virus, with the sera from the mice immunized with 1 μg of TRIPΔU3CMV-sE(WNV) vector particles, by comparison with control sera.

2.2) Analysis by Immunoprecipitation of the Specificity of the Sera from the Immunized Animals The specificity of the sera from the animals immunized with the TRIPΔU3.CMV-sE vector was verified by immunoprecipitation. The sera from the mice immunized with the TRIPΔU3.CMV-sE vector react with the envelope protein E of West Nile virus; the reactivity is stronger at $D_{23}$ than at $D_{14}$ after the vaccine injection (FIG. 3).

2.3) Analysis of the Neutralizing Activity of the Sera From the Immunized Animals, with Respect to West Nile Virus The neutralizing activity of the sera from the mice immunized with a single injection of TRIPΔU3.CMV-sE (WNV) vector particles, with respect to West Nile virus, was verified experimentally by measuring the reduction in viral replication foci (TNRF90) on VERO cells. The titres at $D_{14}$ and $D_{23}$ after vaccine injection are, respectively, 10 and 20 (FIG. 2).

EXAMPLE 3

Analysis of the Protective Capacity of the TRIPΔU3.CMV-sE (WNV) Vector in BALB/c Mice The protective role of the anti-E protein antibodies produced after immunization of mice with TRIPΔU3.CMV-sE (WNV) vector particles was tested in the murine model of WNV-associated encephalitis (Deubel et al., Ann. N.Y. Acad. Sci., 2001, 951, 195-206; Mashimo et al., 2002, precited; International Application WO 02/081511; Ceccaldi et al., FEMS Microbiol. Lett., 2004, 233, 1-6). Thus, mice were challenged by intraperitoneal inoculation of 10 $LD_{50}$ (dose that is lethal in 50% of the mice) or 100 $LD_{50}$ of the highly neuroinvasive and neurovirulent IS-98-ST1 strain of West Nile virus.

More precisely, two challenge protocols were used: (i) the first group of 6 mice immunized as described in Example 2 received 10 $LD_{50}$ of the IS-98-ST1 strain, 15 days after the vaccine injection (D15); (ii) the second group of 6 mice immunized as described in Example 2 received 100 $LD_{50}$ of the IS-98-ST1 strain, 30 days after the vaccine injection (D30). The challenge virus is diluted in DPBS (pH 7.5), supplemented with 0.2% of bovine serum albumin (Sigma); 1 $LD_{50}$ corresponds to 10 $FFU_{AP61}$/ml.

The survival curve for the first group of mice (FIG. 4A) shows that all the control mice, inoculated with DPBS or with the TRIPΔU3.CMV-EGFP vector, die 13 days after the inoculation of the viral challenge dose. On the other hand, the 6 mice immunized with the TRIPΔU3.CMV-sE (WNV) vector are resistant to the lethal dose and showed no morbidity.

Twenty-two days after the challenge, the resistant mice have anti-West Nile virus antibody titres (1.7±0.1, dilution $1:10^4$), by ELISA, that are greater than those obtained before the challenge. The sera from the challenged mice react strongly with the E protein of West Nile virus (FIG. 3) and the neutralizing antibodies have a titre of 100, 1 month after the challenge.

The survival curve for the second group of mice (FIG. 4B) shows that all the control mice, inoculated with DPBS or with the TRIPΔU3.CMV-EGFPs vector (DPBS), die within 9 days following the inoculation of the viral challenge dose. On the other hand, the 6 mice immunized with the TRIPΔU3.CMV-sE (WNV) vector are resistant to the lethal dose and show no morbidity. As in the first group of mice, the sera from the challenged mice react strongly with the E protein of West Nile virus (FIG. 3) and the neutralizing antibodies have a titre of 100, 1 month after the challenge.

In addition, the absence of reactivity of the antibodies from challenged mice, with respect to the non-structural proteins of West Nile virus (FIG. 3), suggest that the protective immunity induced by the TRIPΔU3.CMV-sE (WNV) vector is sufficient to prevent infection with the challenge virus.

The results show that a single injection of a small amount of TRIPΔU3.CMV-sE (WNV) vector particles in adult mice induces, after two weeks of immunization, the production of neutralizing antibodies and confers protective immunity against a lethal challenge with West Nile virus inoculated peripherally.

EXAMPLE 4

Preparation of Viral Pseudoparticles Using the TRIPΔU3.CMV-prM-E (WNV) Recombinant Vector 1) Preparation of the TRIPΔU3.CMV-prM-E (WNV) Vector A recombinant HIV vector of triplex type, comprising a cDNA encoding the prM and E proteins of the IS-98-ST1 strain of West Nile virus, corresponding to positions 399 to 2469 of the sequence of the genome (application FR 01 04599 and Genbank AF481864), was constructed as described in Example 1. Stable lines transduced with the TRIPΔU3.CMV-prM-E (WNV) recombinant vector were obtained as described in Example 1.

2) Preparation of Viral Pseudoparticles or VLPs

The culture supernatant of the cells transduced with the TRIPΔU3.CMV-prM-E (WNV) vector is harvested, and precipitated with PEG 6000 (Fluka, 7% W/V) 4 to 5 hours at 4° C., with gentle agitation. The precipitate obtained is centrifuged for 30 minutes at 9000 rpm at 4° C., and the pellet containing the VLPs is taken up in 4 ml of TNE (20 mM Tris-HCl, pH 8.0; 150 mM NaCl; 2 mM EDTA) and deposited onto a discontinuous sucrose gradient (20%-60% sucrose in 1×TNE). The gradient is centrifuged at 39 000 rpm for 2 h, and the opalescent band at the 20-60% interface is harvested, deposited on a linear gradient (11-55% sucrose in 1×TNE) and centrifuged at 35 000 rpm for 16 h. The gradient fractions are collected (11 fractions of 0.5 ml) and then analyzed by ELISA using an anti-WNV immune serum (1:20), by SDS-PAGE gel electrophoresis and Coomassie blue staining, and by Western blotting using an anti-WNV immune serum. The results of the ELISA, given in FIG. 5, indicate the presence of purified VLPs in fractions 6 to 10 of the gradient.

EXAMPLE 5

Analysis of the Immunogenic and Protective Capacity of the TRIPΔU3.CMV-sE Vector in 129 Mice 1) Materials and Methods 1.1) Immunization/Vaccination Protocol Six to eight week old 129 mice (six groups of six mice) were intraperitoneally (i.p.) inoculated with varying doses of TRIPΔU3.CMV-sE (WNV) vector particles prepared as described in Example 1, diluted in 0.1 ml Dulbecco's PBS (DPBS; pH 7.5) supplemented with 0.2% bovine serum albumin (BSA).

The animals were given a single vaccine injection.

The control groups were inoculated, under the same conditions, with 500 ng p24 antigen equivalent of TRIPΔU3.CMV-GFP vector particles prepared in a similar manner to the TRIPΔU3.CMV-sE (WNV) vector particles (one group of six mice), or DPBS buffer alone (one group of six mice).

Mice were bled periorbitally at 6, 13, 20 or days post-immunization ($D_6$, $D_{13}$, $D_{20}$, $D_{27}$) and pooled sera were heat-inactivated for 30 min at 56° C. before measurement of anti-WNV total antibodies, IgG and IgM, and in vitro neutralizing activity, as described in example 2.

WNV challenge was performed by i.p. inoculation of neurovirulent WNV strain IS-98-ST1, prepared as described in example 2. Animals were subsequently challenged i.p. with 1000 $LD_{50}$ (i.p. $LD_{50}$=10 FFU) of WNV strain IS-98-ST1 at 7 or 14 days post immunization. The challenged mice were monitored daily for signs of morbidity or mortality, for up to 21 days.

1.2) Flow Cytometry Assay 293T cells cultured on 25 cm2 flasks were transduced with TRIPΔU3.CMV-GFP vector particles which have been, either heat-inactivated for 10 min at 70° C., or untreated (positive control). At 48 h, cells were detached, washed and fixed with 2% PFA. The GFP fluorescence intensity was measured by FACSscan and analyzed with CellQuest software.

2) Results

In order to take into account inter-individual immune response variability, 129 mice which are less congenic than BALB/c were selected for assessing the humoral immune response induced by the lentiviral vector expressing WNV-sE.

2.1) Strong Antibody Responses Following Intraperitoneal Injection of TRIPΔU3.CMV-sE Vector Particles.

In 129 adult mice immunized with a single dose of TRIPΔU3.CMV-sE (WNV) vector particles equivalent to 500 ng of p24 antigen, total antibodies against WNV were detectable as early as 6 days post immunization, although present at low concentration. By comparison, no anti-WNV antibodies were detected in sera of TRIPΔU3.CMV-GFP immunized mice. As expected at this time point, the humoral response corresponded to IgM and not IgG antibodies. Total antibody responses increased 10-fold to reach a plateau at day 13, and were then maintained over time. At these later time points (day 13, 20, 27), IgM antibody disappeared, to be replaced by IgG (Table 2).

TABLE 2

Antibody response of mice to inoculation with TRIPΔU3.CMV-sE (WNV)

| Immunizing vector[a], day of bleeding | WNV antibody titer[b] | WNV IgM antibody titer[b] | WNV IgG antibody titer[b] | Anti-WNV FRNT90[c] |
|---|---|---|---|---|
| TRIPΔU3.CMV-GFP | | | | |
| Day 27 | <100 | <100 | <100 | <10 |
| TRIPΔU3.CMV-sE (WNV) | | | | |
| Day 06 | 3 000 | 300 | <100 | 10 |
| Day 13 | 30 000 | <100 | 1 000 | 10 |
| Day 20 | 30 000 | <100 | 1 000 | 10 |
| Day 27 | 30 000 | <100 | 1 000 | 20 |

[a]Groups of adult 129 mice were inoculated i.p. with a quantity of lentiviral vector particles corresponding to 500 ng of p24 antigen
[b]Determined by ELISA on pooled heat-inactivated sera
[c]FRNT: Focus Reduction Neutralization Test: the highest serum dilution that reduced the number of FFU of WNV by least 90%.

These antibodies were reactive with WNV E-glycoprotein from IS-98-ST1 infected Vero cell lysates as demonstrated by RIP assay (FIG. 6A). A focus reduction neutralization test (FRNT) showed that sera from TRIPΔU3.CMV-sE (WNV) immunized mice contained detectable levels of WNV neutralizing antibodies as early as 6 days post-immunization (Table 2). Together these data show that an early and specific anti-WNV antibody immune response is mounted in mice immunized with TRIPΔU3.CMV-sE (WNV) vector particles.

2.2) Early Protection Conferred to Mice by TRIPΔU3.CMV-sE (WNV) Vaccination Against a High-Dose WNV Challenge.

Mice immunized with a single dose of TRIPΔU3.CMV-sE (WNV) vector particles equivalent to 500 ng of p24 antigen were fully protected against a high viral challenge as early as 7 days post-immunization, since no morbidity or mortality were observed in this group (Table 3).

TABLE 3

Rapid protection by TRIPΔU3.CMV-sE (WNV) against WNV infection

| Immunizing vector[a], day of challenge | Protection[b] (n° of surviving/n° of infected) | Post-challenge WNV antibody titer[c] |
|---|---|---|
| DPBS | | |
| Day 7 | 0/2 | ND |
| Day 14 | 0/2 | ND |
| TRIPΔU3.CMV-GFP | | |
| Day 7 | 0/2 | ND |
| Day 14 | 0/2 | ND |
| TRIPΔU3.CMV-sE (WNV) | | |
| Day 7 | 6/6 | 200 000 |
| Day 14 | 6/6 | 300 000 |

[a]Groups of adult 129 mice were inoculated i.p. with a single dose of lentiviral vector particles corresponding to 500 ng of p24 antigen or with DPBS.
[b]At day of challenge, mice were inoculated i.p. with 1,000 i.p. $LD_{50}$ of WNV strain IS-98-ST1. Survivals were recorded for 21 days.
[c]Determined by ELISA on pooled heat-inactivated sera.
ND: not determined The infectious virus dose used in the viral challenge was selected to correspond to the maximal viral inoculum that can be transmitted by a mosquito bite. This dose is estimated to correspond to 10,000 in vitro FFU (Despres et al., J. Infect. Dis., 2005, 191, 207-214; Mashimo et al., 2002, precited), itself corresponding to 1000 in vivo $LD_{50}$ by the intraperitoneal route.

All mice immunized with the control vector TRIPΔU3.CMV-GFP or with DPBS died within 11 days of challenge (Table 3). Interestingly, total antibodies against WNV increased by a factor of ten after challenge, suggesting that an effective secondary response was mounted in TRIPΔU3.CMV-sE (WNV) immunized mice (Table 3). Equivalent results were obtained in BALB/c mice. These results indicate that TRIPΔU3.CMV-sE (WNV) vaccination confers a very quick, fully protective immune response against a high WNV challenge. This could be of major importance in the context of an outbreak where protection of sensitive species is an emergency.

2.3) The Immunity Conferred by the Lentiviral Vector Vaccine is Sterilizing.

To address whether or not WNV primo-infection can take place in vaccinated animals upon challenge, in other words, whether the elicited immune response confers sterilizing protective immunity, RIP assays were performed on pooled sera from immunized mice, collected before and at 21 days after WNV challenge. Sera obtained at day 13, 20 and 27 post-immunization with a single dose of TRIPΔU3.CMV-sE (WNV) vector particles equivalent to 500 ng of p24 antigen, reacted with the E protein of WNV. However, sera obtained from day 6 post-immunization did not react with this protein (FIG. 6A). Since RIP assays are not capable of detecting IgM, this is consistent with the ELISA results that show that at 6 days p.i. only IgM and not IgG antibodies against WNV are present. Sera from TRIPΔU3.CMV-GFP immunized mice did not react with WNV E protein.

Interestingly, no antibodies against any viral protein other than WNV E were detected in post-challenge sera from TRIPΔU3.CMV-sE (WNV) vaccinated mice (FIG. 6B). This absence of antibodies against WNV non-structural proteins, strongly suggests that no viral replication took place in all TRIPΔU3.CMV-sE (WNV) vaccinated mice. Thus, TRIPΔU3.CMV-sE (WNV) vaccination confers full sterilizing immunity to mice.

This could represent an important advantage if the vaccine were to be used for bird-immunization. Indeed, while horses, humans and other mammals are believed to be dead-end hosts of WNV infection, birds are known to be amplifying hosts and participate in the maintenance of an epidemic (Dauphin et al., Comp. Immunol. Microbiol. Infect. Dis., 2004, 27, 343-355).

2.4) Protection Provided by a Single Immunization of TRIPΔU3.CMV-sE (WNV) is Long Lasting.

In order to determine whether a single immunization with the TRIPΔU3.CMV-sE (WNV) lentiviral vector based vaccine has the potential to elicit long-term protective immunity against WNV, pooled sera from the 129 immunized mice were tested by ELISA and FRNT, three months after the injection of the TRIPΔU3.CMV-sE (WNV) vaccine.

Antibody levels in mice immunized with a single dose of TRIPΔU3.CMV-sE (WNV) vector particles equivalent to 500 ng of p24 antigen, were still remarkably high 3 months post injection (1:30,000), and neutralizing antibodies persisted (Table 4).

TABLE 4

Long-term protection by TRIP/$sE_{WNV}$ against WNV infection

| Immunizing vector[a] | WNV antibody titer[b] (pre-challenge) | Anti-WNV FRNT90[c] (pre-challenge) | Protection[d] n° of surviving/ n° of infected | WNV antibody titer[b] (post-challenge) | Anti-WNV FRNT90[c] (post-challenge) |
|---|---|---|---|---|---|
| TRIPΔU3. CMV-GFP | <100 | <10 | 0/3 | ND | ND |
| TRIPΔU3. CMV-sE (WNV) | 30 000 | 20 | 13/13 | 500 000 | 400 |

[a]ng to 500 ng of p24 antigen.
[b]Determined by ELISA on pooled heat-inactivated sera.
[c]FRNT: Focus Reduction Neutralization Test:: the highest serum dilution that reduced the number of FFU of WNV by least 90%.
[d]Mice were inoculated i.p. with 1000 $LD_{50}$ of WNV strain IS-98-ST1, three months post immunization. Survival was recorded for 21 days.

Neither morbidity nor mortality was observed in mice immunized with TRIPΔU3.CMV-sE (WNV) and subsequently challenged i.p. with a 1000 LD$_{50}$ dose of IS-98-ST1 WNV, whereas all control mice died (Table 4). Total antibody titers as well as neutralizing antibodies increased after challenge, suggesting that an effective secondary response was mounted in mice immunized with a TRIPΔU3.CMV-sE (WNV) three month earlier (Table 4). This shows that a single immunization with the WNV-sE coding lentiviral vector is enough to provide for a long lasting protective immunity in mice.

2.5) A Single Minute Dose of TRIPΔU3.CMV-sE (WNV) is Enough to Confer Full and Rapid Protection.

To calculate the minimal dose of vector required to achieve full protective immunity, several groups of 129 mice were immunized i.p. with decreasing doses of TRIPΔU3.CMV-sE (WNV) or a 500 ng dose of TRIPΔU3.CMV-GFP vector particles as a control. Seven days later, all mice were challenged with 1000 LD$_{50}$ IS-98-ST1. As expected, all mice that received the control vector died within 11-13 days of challenge. Results showed that the minimal dose of TRIPΔU3.CMV-sE (WNV) required for full protection of mice was a vector particle quantity equivalent to 50 ng of p24 antigen (Table 5).

TABLE 5

Dose-dependent protection by TRIP/sE$_{WNV}$ against WNV infection

| Immunizing vector[a], dose (ng of p24) | Protection[b] n° of surviving/n° of infected | Post-challenge WNV antibody titer[c] |
|---|---|---|
| TRIPΔU3.CMV-GFP | | |
| 500 | 0/6 | ND |
| Heat-inactivated TRIPΔU3.CMV-sE (WNV)[d] | | |
| 50 | 0/6 | ND |
| TRIPΔU3.CMV-sE (WNV) | | |
| 500 | 6/6 | 200 000 |
| 150 | 6/6 | 300 000 |
| 50 | 12/12 | 300 000 |
| 15 | 5/6 | 300 000 |
| 5 | 2/5 | 200 000 |
| 1.5 | 11/12 | ND |

[a]Groups of adult 129 mice were inoculated i.p. with a single dose of lentiviral vector particles.
[b]Mice were inoculated i.p. with 1,000 i.p. LD$_{50}$ of WNV strain IS-98-ST1 one week after priming. Survival was recorded for 21 days.
[c]Determined by ELISA on pooled heat-inactivated sera.
[d]Lentiviral vector particles were heat-inactivated for 10 min at 70° C.

Lower doses conferred only partial protection thus allowing to calculate the 50% protective dose to be the vector particle equivalent of 6.2 ng of p24 antigen. Of note, these dose-protection experiments were performed in the most stringent challenge conditions, with an early challenge at day 7 post-vaccination and with a high virus challenge inoculum (1000 LD$_{50}$). Owing that total antibody concentrations increases by a ten-fold factor between day and 15, it is probable that the 50% protective dose would have been even lower than 6.2 ng if calculated only one week later. Immune sera from mice that received the vector particle equivalent of 50 ng of p24 of TRIPΔU3.CMV-sE (WNV) had no detectable anti-WNV antibodies. Given that such low amount of TRIPΔU3.CMV-sE confers full protection one week after priming, one might predict that the lentiviral vector based vaccine must generate signals that initiate innate immunity to WNV.

Furthermore, it is important to note that the dose required for full protective immunity could have been sub-evaluated due to the model used. Indeed, it has been shown that mice cells have a lower permissivity to lentiviral vector transduction than other mammal cells, including human cells (Giannini et al., Hepatology, 2003, 38, 114-122; Nguyen et al., Mol. Ther., 2002, 6, 199-209). Avian cells show a better permissivity to transduction than murine cells allowing to predict that minute lentiviral vector vaccine doses would be effective in fowl.

In order to make sure that the protection obtained was specifically due to the actual vector-mediated expression of the WNV-sE antigen and not to residual WNV-sE protein or vector plasmid DNA contaminating the vector stock. Thus, mice were immunized with heat-inactivated (10 min at 70° C.) TRIPΔU3.CMV-sE (WNV) vector particles, a treatment that abrogates transduction (FIG. 7). After WNV challenge, all mice injected with the heat-inactivated TRIPΔU3.CMV-sE (WNV) died (Table 5). It is therefore unlikely that free naked DNA plays a role in protection.

In addition, by virtue of the ubiquitous tropism of the VSV-G envelope used for pseudotyping the vector particles the lentiviral vector vaccine can theoretically be used, with no modification, in any vertebrate species, including humans and animals like horses, fowl, and zoo mammals at risk.

These results demonstrate that a minute dose of vector particles is enough to achieve quick and fully protective immunity in mice. This makes this candidate vaccine interestingly cost-effective, and allows the set up of protocols for mass vaccination (for instance via aerosols), in poultry stock or horse breeding farms.

The invention claimed is:

1. A method for inducing a protective humoral immune response against a West Nile virus with a lentiviral vector comprising administering a lentiviral vector encoding a secreted, truncated envelope glycoprotein of a West Nile virus, from which the membrane anchoring region has been removed,
   wherein the lentiviral vector comprises a lentiviral central polypurine tract and cis-acting region for termination, to a non-human animal, and
   wherein the administration induces a protective humoral immune response against the West Nile virus.

2. The method of claim 1, wherein the lentiviral vector encodes a signal peptide of a West Nile virus M protein precursor protein.

3. The method of claim 1, wherein the lentiviral vector encodes the amino acid sequence of SEQ ID NO:17.

4. The method of claim 1, wherein the lentiviral vector comprises a 3' LTR in which the promoter and activator have been deleted from the U3 region.

5. The method of claim 2, wherein the lentiviral vector comprises a 3' LTR in which the promoter and activator have been deleted from the U3region.

6. The method of claim 3, wherein the lentiviral vector comprises a 3' LTR in which the promoter and activator have been deleted from the U3region.

7. The method of claim 1, wherein the animal is a fowl.
8. The method of claim 1, wherein the animal is a horse.
9. The method of claim 2, wherein the animal is a fowl.
10. The method of claim 2, wherein the animal is a horse.
11. The method of claim 3, wherein the animal is a fowl.
12. The method of claim 3, wherein the animal is a horse.
13. The method of claim 4 wherein the animal is a fowl.
14. The method of claim 4, wherein the animal is a horse.

* * * * *

SEQUENCE LISTING

<160> NUMBER OF SEQ ID NOS: 27

<210> SEQ ID NO 1
<211> LENGTH: 100
<212> TYPE: PRT
<213> ORGANISM: Flavivirus sp.

<400> SEQUENCE: 1

Lys Gly Met Ser Tyr Val Met Cys Thr Gly Ser Phe Lys Leu Glu Lys
1               5                   10                  15

-continued

```
Glu Val Ala Glu Thr Gln His Gly Thr Val Leu Val Gln Val Lys Tyr
            20                  25                  30

Glu Gly Thr Asp Ala Pro Cys Lys Ile Pro Phe Ser Thr Gln Asp Glu
        35                  40                  45

Lys Gly Val Thr Gln Asn Gly Arg Leu Ile Thr Ala Asn Pro Ile Val
    50                  55                  60

Thr Asp Lys Glu Lys Pro Ile Asn Ile Glu Thr Glu Pro Pro Phe Gly
65                  70                  75                  80

Glu Ser Tyr Ile Ile Val Gly Ala Gly Glu Lys Ala Leu Lys Leu Ser
                85                  90                  95

Trp Phe Lys Arg
            100

<210> SEQ ID NO 2
<211> LENGTH: 100
<212> TYPE: PRT
<213> ORGANISM: Flavivirus sp.

<400> SEQUENCE: 2

Lys Gly Met Ser Tyr Ser Met Cys Thr Gly Lys Phe Lys Val Val Lys
1               5                   10                  15

Glu Ile Ala Glu Thr Gln His Gly Thr Ile Val Ile Arg Val Gln Tyr
            20                  25                  30

Glu Gly Asp Gly Ser Pro Cys Lys Thr Pro Phe Glu Ile Met Asp Leu
        35                  40                  45

Glu Lys Arg His Val Leu Gly Arg Leu Thr Thr Val Asn Pro Ile Val
    50                  55                  60

Thr Glu Lys Asp Ser Pro Val Asn Ile Glu Ala Glu Pro Pro Phe Gly
65                  70                  75                  80

Asp Ser Tyr Ile Ile Gly Val Gly Glu Pro Gly Gln Leu Lys Leu Asp
                85                  90                  95

Trp Phe Lys Lys
            100

<210> SEQ ID NO 3
<211> LENGTH: 100
<212> TYPE: PRT
<213> ORGANISM: Flavivirus sp.

<400> SEQUENCE: 3

Lys Gly Met Ser Tyr Ala Met Cys Leu Asn Thr Phe Val Leu Lys Lys
1               5                   10                  15

Glu Ser Glu Glu Thr Gln His Gly Thr Ile Leu Val Lys Val Glu Tyr
            20                  25                  30

Lys Gly Glu Asp Ala Pro Cys Lys Ile Pro Phe Ser Thr Glu Asp Gly
        35                  40                  45

Gln Gly Lys Ala His Asn Gly Arg Leu Ile Thr Ala Asn Pro Val Val
    50                  55                  60

Thr Lys Lys Glu Lys Pro Val Asn Ile Glu Ala Glu Pro Pro Phe Gly
65                  70                  75                  80

Glu Ser Asn Ile Val Ile Gly Ile Gly Asp Lys Ala Leu Lys Ile Asn
                85                  90                  95

Trp Tyr Arg Lys
            100

<210> SEQ ID NO 4
<211> LENGTH: 99
<212> TYPE: PRT

<213> ORGANISM: Flavivirus sp.

<400> SEQUENCE: 4

```
Lys Gly Met Ser Tyr Thr Met Cys Ser Gly Lys Phe Ser Ile Asp Lys
1               5                   10                  15

Glu Met Ala Glu Thr Gln His Gly Thr Thr Val Val Lys Val Lys Tyr
            20                  25                  30

Glu Gly Ala Gly Ala Pro Cys Lys Val Ile Glu Ile Arg Asp Val Asn
        35                  40                  45

Lys Glu Lys Val Val Gly Arg Ile Ile Ser

```
<210> SEQ ID NO 7
<211> LENGTH: 98
<212> TYPE: PRT
<213> ORGANISM: Hepatitis C virus

<400> SEQUENCE: 7

Ala His Phe Leu Asn Leu Lys Glu Lys Pro Lys Glu Thr Pro Ser Val
1               5                   10                  15

Ala His Arg Thr Ser Ser Arg Val Ala Asp Arg Ser Leu Val Glu
                20                  25                  30

Tyr Thr Cys Cys Arg Ala Gly Ala His Asp Trp Val Cys Ala Arg Arg
            35                  40                  45

Val Lys Leu Leu Asn Gly His Ser Leu Ala Asp Asp Ser Leu Ser
    50                  55                  60

Pro Arg Arg Val Gly Ala Lys Ala Gly Pro Gly Leu Ser Pro Gly Thr
65                  70                  75                  80

Leu Gly Pro Ser Met Val Thr Arg Ala Ala Gly Gln Gly Gly Gly Ser
                85                  90                  95

Cys Pro

<210> SEQ ID NO 8
<211> LENGTH: 98
<212> TYPE: PRT
<213> ORGANISM: Hepatitis C virus

<400> SEQUENCE: 8

Ala Gln Ile Leu Asn Leu Lys Glu Lys Pro Lys Glu Thr Gln Thr Ala
1               5                   10                  15

Ala His Arg Thr Leu Ser Ser Arg Val Ala Val Arg Ser Leu Ala Glu
                20                  25                  30

Phe Thr Cys Cys Arg Ala Gly Ala Pro Gly Trp Val Cys Ala Arg Gln
            35                  40                  45

Gly Arg Leu Leu Ser Asp Pro Ser Arg Val Asp Asp Ala Ser Pro Ser
    50                  55                  60

Arg Lys Ile Gly Ala Pro Pro Ala Ser Pro Gly Glu Ser Gln Asp Ile
65                  70                  75                  80

Leu Gly Pro Cys Thr Glu Thr Arg Val Ala Ala Gly Arg Val Gly Ser
                85                  90                  95

Cys Pro

<210> SEQ ID NO 9
<211> LENGTH: 98
<212> TYPE: PRT
<213> ORGANISM: Hepatitis C virus

<400> SEQUENCE: 9

Ala Arg Ile Leu Asn Leu Lys Glu Lys Pro Asn Val Thr Pro Thr Ala
1               5                   10                  15

Ala His Arg Thr Leu Ser Ser Arg Val Ala Ala Arg Ser Leu Ala Glu
                20                  25                  30

Phe Thr Cys Cys Arg Ala Gly Ala Pro Glu Trp Val Cys Ala Arg Arg
            35                  40                  45

Gly Arg Leu Pro Ser Gly Arg Asn Leu Ala Gly Gly Val Ser Leu Phe
    50                  55                  60

Pro Arg Pro Ala Asp Pro Arg Glu Gly Pro Gly Arg Ser Pro Gly Thr
65                  70                  75                  80

Leu Gly Pro Ser Met Ala Thr Arg Ala Val Gly Gly Arg Asp Pro Ser
```

```
                    85                  90                  95

Cys Pro

<210> SEQ ID NO 10
<211> LENGTH: 98
<212> TYPE: PRT
<213> ORGANISM: Hepatitis C virus

<400> SEQUENCE: 10

Ala Gln Ile Leu Asn Leu Lys Glu Lys Pro Lys Glu Thr Pro Thr Val
1               5                   10                  15

Ala His Lys Thr Leu Ser Phe Arg Ala Ala Arg Ser Leu Ala Glu
                20                  25                  30

Tyr Thr Cys Cys Arg Ala Gly Ala Pro Gly Trp Val Cys Ala Arg Gln
            35                  40                  45

Gly Arg Leu Arg Ser Gly Pro Ser His Val Glu Gly Ala Ser Pro Ser
    50                  55                  60

Leu Arg Ile Gly Ala Pro Leu Ala Asn Pro Gly Glu Asn Gln Asp Thr
65                  70                  75                  80

Pro Gly Pro Tyr Thr Gly Met Arg Asp Ser Ala Gly Gln Asp Arg Ser
                85                  90                  95

Cys Pro

<210> SEQ ID NO 11
<211> LENGTH: 98
<212> TYPE: PRT
<213> ORGANISM: Hepatitis C virus

<400> SEQUENCE: 11

Ala Gln Ile Gln Asn Pro Lys Asp Lys Pro Lys Glu Thr Pro Thr Val
1               5                   10                  15

Ala His Arg Thr Ser Ser Ser Arg Ala Val Val Arg Ser Trp Val Glu
                20                  25                  30

Tyr Thr Cys Cys Arg Ala Gly Ala Leu Asp Trp Val Cys Ala Arg Leu
            35                  40                  45

Gly Arg Leu Pro Asn Gly Pro Ser Pro Glu Ala Gly Val Ser Pro Phe
    50                  55                  60

Gln Arg Leu Ala Ala Arg Arg Ala Val Pro Gly Val Ser Leu Gly Thr
65                  70                  75                  80

His Gly Pro Cys Met Gly Met Arg Ala Ala Gly Gly Gln Gly Gly Ser
                85                  90                  95

Cys Pro

<210> SEQ ID NO 12
<211> LENGTH: 98
<212> TYPE: PRT
<213> ORGANISM: Hepatitis C virus

<400> SEQUENCE: 12

Ala Arg Ile Leu Asn Leu Lys Glu Lys Pro Asn Val Thr Pro Thr Ala
1               5                   10                  15

Ala Gln Trp Thr Leu Ser Ser Arg Val Val Ala Arg Ser Leu Ala Glu
                20                  25                  30

Phe Thr Cys Cys Arg Ala Gly Ala Pro Asp Trp Val Cys Ala Arg Leu
            35                  40                  45

Gly Arg Leu Arg Ser Gly Arg Asn Leu Val Glu Asp Ala Asn Leu Ser
    50                  55                  60
```

-continued

```
Pro Arg Arg Val Asp Pro Arg Glu Gly Pro Gly His Asn Gln Asp Ile
 65                  70                  75                  80

His Gly Leu Phe Thr Val Met Arg Val Val Gly Gln Asp Gly Ser
                 85                  90                  95

Cys Pro

<210> SEQ ID NO 13
<211> LENGTH: 98
<212> TYPE: PRT
<213> ORGANISM: Hepatitis C virus

<400> SEQUENCE: 13

Ala Gln Ile Leu Asn Leu Lys Glu Lys Pro Asn Val Thr Pro Thr Ala
  1               5                  10                  15

Ala His Arg Thr Ser Ser Arg Ala Val Val Arg Ser Leu Val Glu
             20                  25                  30

Phe Thr Cys Cys Arg Ala Gly Ala Pro Gly Trp Val Cys Ala Arg Leu
             35                  40                  45

Gly Arg Leu Pro Ser Gly Arg Asn Leu Val Glu Gly Asp Asn Leu Ser
         50                  55                  60

Pro Arg Phe Ala Gly Pro Arg Ala Gly Pro Gly Leu Ser Pro Gly Thr
 65                  70                  75                  80

Leu Gly Pro Ser Met Ala Met Arg Val Trp Gly Gly Gln Asp Gly Ser
                 85                  90                  95

Cys His

<210> SEQ ID NO 14
<211> LENGTH: 160
<212> TYPE: PRT
<213> ORGANISM: Hepatitis C virus

<400> SEQUENCE: 14

Ala Arg Ile Leu Asn Leu Lys Lys Lys Thr Asn Val Thr Pro Thr Val
  1               5                  10                  15

Ala His Arg Thr Ser Ser Arg Val Ala Val Arg Ser Leu Val Glu
             20                  25                  30

Phe Thr Cys Cys Arg Ala Gly Ala Leu Asp Trp Val Cys Ala Arg Arg
             35                  40                  45

Glu Arg Leu Pro Ser Gly Arg Asn Leu Glu Val Asp Val Ser Leu Ser
         50                  55                  60

Pro Arg Leu Val Gly Pro Arg Ala Gly Pro Gly Leu Ser Pro Gly Thr
 65                  70                  75                  80

Leu Gly Pro Ser Met Ala Met Arg Ala Ala Gly Gly Arg Asp Gly Ser
                 85                  90                  95

Cys Leu Pro Val Ala Leu Gly Leu Ala Gly Ala Pro Gln Thr Pro Gly
             100                 105                 110

Val Gly Arg Ala Ile Trp Val Arg Ser Ser Ile Pro Leu Arg Ala Ala
             115                 120                 125

Ser Pro Thr Ser Trp Gly Thr Tyr Arg Ser Ser Ala Pro Leu Leu Glu
         130                 135                 140

Ala Leu Pro Gly Pro Trp Arg Met Ala Ser Gly Phe Trp Lys Thr Ala
145                 150                 155                 160

<210> SEQ ID NO 15
<211> LENGTH: 4555
<212> TYPE: DNA
<213> ORGANISM: artificial sequence
<220> FEATURE:
```

<223> OTHER INFORMATION: plasmid

<400> SEQUENCE: 15

```
tggaagggct aattcactcc caacgaagac aagatatcct tgatctgtgg atctaccaca      60
cacaaggcta cttccctgat tagcagaact acacaccagg gccagggatc agatatccac     120
tgacctttgg atggtgctac aagctagtac cagttgagcc agagaagtta aagaagcca     180
acaaaggaga gaacaccagc ttgttacaac ctgtgagcct gcatgggatg gatgacccgg     240
agagagaagt gttagagtgg aggtttgaca gccgcctagc atttcatcac ggtggcccga     300
gagctgcatc cggagtactt caagaactgc tgatatcgag cttgctacaa gggactttcc     360
gctgggggac tttccaggga ggcgtggcct gggcgggact ggggagtggc gagccctcag     420
atcctgcata taagcagctg ctttttgcct gtactgggtc tctctggtta gaccagatct     480
gagcctggga gctctctggc taactaggga acccactgct taagcctcaa taaagcttgc     540
cttgagtgct tcaagtagtg tgtgcccgtc tgttgtgtga ctctggtaac tagagatccc     600
tcagaccctt ttagtcagtg tggaaaatct ctagcagtgg cgcccgaaca gggacttgaa     660
agcgaagggg aaaccagagg agctctctcg acgcaggact cggcttgctg aagcgcggaa     720
ttccgcgcca cggcaagagg cgaggggcgg cgactggtga gtacgccaaa aattttgact     780
agcggaggct agaaggagag atgggtgcg agagcgtca gtattaagcg ggggagaatt     840
agatcgcgat gggaaaaaat tcggttaagg ccaggggaa agaaaaata taaattaaaa     900
catatagtat gggcaagcag ggagctagaa cgattcgcag ttaatcctgg cctgttagaa     960
acatcagaag gctgtagaca aatactggga cagctacaac catcccttca gacaggatca    1020
gaagaactta gatcattata taatacagta gcaaccctct attgtgtgca tcaaaggata    1080
gagataaaag acaccaagga agctttagac aagatagagg aagagcaaaa caaaagtaag    1140
accaccgcac agcaagcggc cgctgatctt cagacctgga ggaggagata tgagggacaa    1200
ttggagaagt gaattatata aatataaagt agtaaaaatt gaaccattag gagtagcacc    1260
caccaaggca aagagaagag tggtgcagag agaaaaaaga gcagtgggaa taggagcttt    1320
gttccttggg ttcttgggag cagcaggaag cactatgggc gcagcgtcaa tgacgctgac    1380
ggtacaggcc agacaattat tgtctggtat agtgcagcag cagaacaatt tgctgagggc    1440
tattgaggcg caacagcatc tgttgcaact cacagtctgg ggcatcaagc agctccaggc    1500
aagaatcctg gctgtggaaa gatacctaaa ggatcaacag ctcctgggga tttggggttg    1560
ctctggaaaa ctcatttgca ccactgctgt gccttggaat gctagttgga gtaataaatc    1620
tctggaacag atttggaatc acacgacctg gatggagtgg gacagagaaa ttaacaatta    1680
cacaagctta atacactcct taattgaaga atcgcaaaac cagcaagaaa agaatgaaca    1740
agaattattg gaattagata atgggcaag tttgtggaat tggtttaaca taacaaattg    1800
gctgtggtat ataaaattat tcataatgat agtaggaggc ttggtaggtt taagaatagt    1860
ttttgctgta ctttctatag tgaatagagt taggcaggga tattcaccat tatcgtttca    1920
gacccacctc ccaaccccga ggggacccga caggcccgaa ggaatagaag aagaaggtgg    1980
agagagagac agagacagat ccattcgatt agtgaacgga tctcgacggt atcgccgaat    2040
tcacaaatgg cagtattcat ccacaatttt aaaagaaaag ggggattgg ggggtacagt    2100
gcagggaaa gaatagtaga cataatagca acagacatac aaactaaaga attacaaaaa    2160
caaattacaa aaattcaaaa ttttcgggtt tattacaggg acagcagaga tccactttgg    2220
ggcgataagc ttgggagttc cgcgttacat aacttacggt aaatggcccg cctggctgac    2280
```

-continued

```
cgcccaacga cccccgccca ttgacgtcaa taatgacgta tgttcccata gtaacgccaa      2340
tagggacttt ccattgacgt caatgggtgg agtatttacg gtaaactgcc cacttggcag      2400
tacatcaagt gtatcatatg ccaagtacgc ccctattga cgtcaatgac ggtaaatggc       2460
ccgcctggca ttatgcccag tacatgacct tatgggactt tcctacttgg cagtacatct      2520
acgtattagt catcgctatt accatggtga tgcggttttg gcagtacatc aatgggcgtg      2580
gatagcggtt tgactcacgg ggatttccaa gtctccaccc cattgacgtc aatgggagtt      2640
tgttttggca ccaaaatcaa cgggactttc caaaatgtcg taacaactcc gccccattga      2700
cgcaaatggg cggtaggcgt gtacggtggg aggtctatat aagcagagct cgtttagtga      2760
accgtcagat cgcctggaga cgccatccac gctgttttga cctccataga agacaccgac      2820
tctagaggac gtacgatgag agttgtgttt gtcgtgctat tgcttttggt ggccccagct      2880
tacagcttca actgccttgg aatgagcaac agagacttct tggaaggagt gtctggagca      2940
acatgggtgg atttggttct cgaaggcgac agctgcgtga ctatcatgtc taaggacaag      3000
cctaccatcg atgtgaagat gatgaatatg gaggcggtca acctggcaga ggtccgcagt      3060
tattgctatt tggctaccgt cagcgatctc tccaccaaag ctgcgtgccc gaccatggga      3120
gaagctcaca atgacaaacg tgctgaccca gcttttgtgt gcagacaagg agtggtggac      3180
aggggctggg gcaacggctg cggattattt ggcaaaggaa gcattgacac atgcgccaaa      3240
tttgcctgct ctaccaaggc aataggaaga accatcttga aagagaatat caagtacgaa      3300
gtggccattt tgtccatgg accaactact gtggagtcgc acggaaacta ctccacacag      3360
gttggagcca ctcaggcagg gagattcagc atcactcctg cggcgccttc atacacacta      3420
aagcttggag aatatggaga ggtgacagtg gactgtgaac cacggtcagg gattgacacc      3480
aatgcatact acgtgatgac tgttggaaca aagacgttct tggtccatcg tgagtggttc      3540
atggacctca acctcccttg gagcagtgct ggaagtactg tgtggaggaa cagagagacg      3600
ttaatggagt ttgaggaacc acacgccacg aagcagtctg tgatagcatt gggctcacaa      3660
gagggagctc tgcatcaagc tttggctgga gccattcctg tggaattttc aagcaacact      3720
gtcaagttga cgtcgggtca tttgaagtgt agagtgaaga tggaaaaatt gcagttgaag      3780
ggaacaacct atggcgtctg ttcaaaggct ttcaagtttc ttgggactcc cgcagacaca      3840
ggtcacggca ctgtggtgtt ggaattgcag tacactggca cggatggacc ttgcaaagtt      3900
cctatctcgt cagtggcttc attgaacgac ctaacgccag tgggcagatt ggtcactgtc      3960
aaccctttg tttcagtggc cacgccaac gctaaggtcc tgattgaatt ggaaccaccc      4020
tttggagact catacatagt ggtgggcaga ggagaacaac agatcaatca ccattggcac      4080
aagtctggaa gcagcattgg caaagccttt acaaccaccc tcaaaggagc gcagagacta      4140
gccgctctag agacacagc ttgggacttt ggatcagttg gaggggtgtt cacctcagtt      4200
gggaaggctg tctaatgcgc gcggtacctt taagaccaat gacttacaag gcagctgtag      4260
atcttagcca cttttaaaa gaaaaggggg gactggaagg gctaattcac tcccaacgaa      4320
gacaagatcg tcgagagatg ctgcatataa gcagctgctt tttgcttgta ctgggtctct      4380
ctggttagac cagatctgag cctgggagct ctctggctaa ctagggaacc cactgcttaa      4440
gcctcaataa agcttgcctt gagtgcttca agtagtgtgt gcccgtctgt tgtgtgactc      4500
tggtaactag agatccctca gacccttttta gtcagtgtgg aaaatctcta gcagt         4555
```

<210> SEQ ID NO 16
<211> LENGTH: 1393
<212> TYPE: DNA

-continued

```
<213> ORGANISM: Flavivirus sp.
<220> FEATURE:
<221> NAME/KEY: CDS
<222> LOCATION: (7)..(1386)

<400> SEQUENCE: 16 cgtacg atg aga gtt gtg ttt gtc gtg cta ttg ctt ttg gtg gcc cca        48
       Met Arg Val Val Phe Val Val Leu Leu Leu Leu Val Ala Pro
       1               5                   10 gct tac agc ttc aac tgc ctt gga atg agc aac aga gac ttc ttg gaa       96
Ala Tyr Ser Phe Asn Cys Leu Gly Met Ser Asn Arg Asp Phe Leu Glu
15                  20                  25                  30 gga gtg tct gga gca aca tgg gtg gat ttg gtt ctc gaa ggc gac agc      144
Gly Val Ser Gly Ala Thr Trp Val Asp Leu Val Leu Glu Gly Asp Ser
                35                  40                  45 tgc gtg act atc atg tct aag gac aag cct acc atc gat gtg aag atg      192
Cys Val Thr Ile Met Ser Lys Asp Lys Pro Thr Ile Asp Val Lys Met
            50                  55                  60 atg aat atg gag gcg gtc aac ctg gca gag gtc cgc agt tat tgc tat      240
Met Asn Met Glu Ala Val Asn Leu Ala Glu Val Arg Ser Tyr Cys Tyr
        65                  70                  75 ttg gct acc gtc agc gat ctc tcc acc aaa gct gcg tgc ccg acc atg      288
Leu Ala Thr Val Ser Asp Leu Ser Thr Lys Ala Ala Cys Pro Thr Met
    80                  85                  90 gga gaa gct cac aat gac aaa cgt gct gac cca gct ttt gtg tgc aga      336
Gly Glu Ala His Asn Asp Lys Arg Ala Asp Pro Ala Phe Val Cys Arg
95                  100                 105                 110 caa gga gtg gtg gac agg ggc tgg ggc aac ggc tgc gga tta ttt ggc      384
Gln Gly Val Val Asp Arg Gly Trp Gly Asn Gly Cys Gly Leu Phe Gly
                115                 120                 125 aaa gga agc att gac aca tgc gcc aaa ttt gcc tgc tct acc aag gca      432
Lys Gly Ser Ile Asp Thr Cys Ala Lys Phe Ala Cys Ser Thr Lys Ala
            130                 135                 140 ata gga aga acc atc ttg aaa gag aat atc aag tac gaa gtg gcc att      480
Ile Gly Arg Thr Ile Leu Lys Glu Asn Ile Lys Tyr Glu Val Ala Ile
        145                 150                 155 ttt gtc cat gga cca act act gtg gag tcg cac gga aac tac tcc aca      528
Phe Val His Gly Pro Thr Thr Val Glu Ser His Gly Asn Tyr Ser Thr
    160                 165                 170 cag gtt gga gcc act cag gca ggg aga ttc agc atc act cct gcg gcg      576
Gln Val Gly Ala Thr Gln Ala Gly Arg Phe Ser Ile Thr Pro Ala Ala
175                 180                 185                 190 cct tca tac aca cta aag ctt gga gaa tat gga gag gtg aca gtg gac      624
Pro Ser Tyr Thr Leu Lys Leu Gly Glu Tyr Gly Glu Val Thr Val Asp
                195                 200                 205 tgt gaa cca cgg tca ggg att gac acc aat gca tac tac gtg atg act      672
Cys Glu Pro Arg Ser Gly Ile Asp Thr Asn Ala Tyr Tyr Val Met Thr
            210                 215                 220 gtt gga aca aag acg ttc ttg gtc cat cgt gag tgg ttc atg gac ctc      720
Val Gly Thr Lys Thr Phe Leu Val His Arg Glu Trp Phe Met Asp Leu
        225                 230                 235 aac ctc cct tgg agc agt gct gga agt act gtg tgg agg aac aga gag      768
Asn Leu Pro Trp Ser Ser Ala Gly Ser Thr Val Trp Arg Asn Arg Glu
    240                 245                 250 acg tta atg gag ttt gag gaa cca cac gcc acg aag cag tct gtg ata      816
Thr Leu Met Glu Phe Glu Glu Pro His Ala Thr Lys Gln Ser Val Ile
255                 260                 265                 270 gca ttg ggc tca caa gag gga gct ctg cat caa gct ttg gct gga gcc      864
Ala Leu Gly Ser Gln Glu Gly Ala Leu His Gln Ala Leu Ala Gly Ala
                275                 280                 285 att cct gtg gaa ttt tca agc aac act gtc aag ttg acg tcg ggt cat      912
```

-continued

```
Ile Pro Val Glu Phe Ser Ser Asn Thr Val Lys Leu Thr Ser Gly His
            290                 295                 300 ttg aag tgt aga gtg aag atg gaa aaa ttg cag ttg aag gga aca acc      960
Leu Lys Cys Arg Val Lys Met Glu Lys Leu Gln Leu Lys Gly Thr Thr
        305                 310                 315 tat ggc gtc tgt tca aag gct ttc aag ttt ctt ggg act ccc gca gac     1008
Tyr Gly Val Cys Ser Lys Ala Phe Lys Phe Leu Gly Thr Pro Ala Asp
    320                 325                 330 aca ggt cac ggc act gtg gtg ttg gaa ttg cag tac act ggc acg gat     1056
Thr Gly His Gly Thr Val Val Leu Glu Leu Gln Tyr Thr Gly Thr Asp
335                 340                 345                 350 gga cct tgc aaa gtt cct atc tcg tca gtg gct tca ttg aac gac cta     1104
Gly Pro Cys Lys Val Pro Ile Ser Ser Val Ala Ser Leu Asn Asp Leu
                355                 360                 365 acg cca gtg ggc aga ttg gtc act gtc aac cct ttt gtt tca gtg gcc     1152
Thr Pro Val Gly Arg Leu Val Thr Val Asn Pro Phe Val Ser Val Ala
            370                 375                 380 acg gcc aac gct aag gtc ctg att gaa ttg gaa cca ccc ttt gga gac     1200
Thr Ala Asn Ala Lys Val Leu Ile Glu Leu Glu Pro Pro Phe Gly Asp
        385                 390                 395 tca tac ata gtg gtg ggc aga gga gaa caa cag atc aat cac cat tgg     1248
Ser Tyr Ile Val Val Gly Arg Gly Glu Gln Gln Ile Asn His His Trp
    400                 405                 410 cac aag tct gga agc agc att ggc aaa gcc ttt aca acc acc ctc aaa     1296
His Lys Ser Gly Ser Ser Ile Gly Lys Ala Phe Thr Thr Thr Leu Lys
415                 420                 425                 430 gga gcg cag aga cta gcc gct cta gga gac aca gct tgg gac ttt gga     1344
Gly Ala Gln Arg Leu Ala Ala Leu Gly Asp Thr Ala Trp Asp Phe Gly
                435                 440                 445 tca gtt gga ggg gtg ttc acc tca gtt ggg aag gct gtc taa tgcgcgc     1393
Ser Val Gly Gly Val Phe Thr Ser Val Gly Lys Ala Val
            450                 455

<210> SEQ ID NO 17
<211> LENGTH: 459
<212> TYPE: PRT
<213> ORGANISM: Flavivirus sp.

<400> SEQUENCE: 17

Met Arg Val Val Phe Val Val Leu Leu Leu Leu Val Ala Pro Ala Tyr
1               5                   10                  15

Ser Phe Asn Cys Leu Gly Met Ser Asn Arg Asp Phe Leu Glu Gly Val
            20                  25                  30

Ser Gly Ala Thr Trp Val Asp Leu Val Leu Glu Gly Asp Ser Cys Val
        35                  40                  45

Thr Ile Met Ser Lys Asp Lys Pro Thr Ile Asp Val Lys Met Met Asn
    50                  55                  60

Met Glu Ala Val Asn Leu Ala Glu Val Arg Ser Tyr Cys Tyr Leu Ala
65                  70                  75                  80

Thr Val Ser Asp Leu Ser Thr Lys Ala Ala Cys Pro Thr Met Gly Glu
                85                  90                  95

Ala His Asn Asp Lys Arg Ala Asp Pro Ala Phe Val Cys Arg Gln Gly
            100                 105                 110

Val Val Asp Arg Gly Trp Gly Asn Gly Cys Gly Leu Phe Gly Lys Gly
        115                 120                 125

Ser Ile Asp Thr Cys Ala Lys Phe Ala Cys Ser Thr Lys Ala Ile Gly
    130                 135                 140

Arg Thr Ile Leu Lys Glu Asn Ile Lys Tyr Glu Val Ala Ile Phe Val
145                 150                 155                 160
```

```
His Gly Pro Thr Thr Val Glu Ser His Gly Asn Tyr Ser Thr Gln Val
            165                 170                 175
Gly Ala Thr Gln Ala Gly Arg Phe Ser Ile Thr Pro Ala Ala Pro Ser
        180                 185                 190
Tyr Thr Leu Lys Leu Gly Glu Tyr Gly Glu Val Thr Val Asp Cys Glu
            195                 200                 205
Pro Arg Ser Gly Ile Asp Thr Asn Ala Tyr Tyr Val Met Thr Val Gly
    210                 215                 220
Thr Lys Thr Phe Leu Val His Arg Glu Trp Phe Met Asp Leu Asn Leu
225                 230                 235                 240
Pro Trp Ser Ser Ala Gly Ser Thr Val Trp Arg Asn Arg Glu Thr Leu
                245                 250                 255
Met Glu Phe Glu Glu Pro His Ala Thr Lys Gln Ser Val Ile Ala Leu
            260                 265                 270
Gly Ser Gln Glu Gly Ala Leu His Gln Ala Leu Ala Gly Ala Ile Pro
        275                 280                 285
Val Glu Phe Ser Ser Asn Thr Val Lys Leu Thr Ser Gly His Leu Lys
    290                 295                 300
Cys Arg Val Lys Met Glu Lys Leu Gln Leu Lys Gly Thr Thr Tyr Gly
305                 310                 315                 320
Val Cys Ser Lys Ala Phe Lys Phe Leu Gly Thr Pro Ala Asp Thr Gly
                325                 330                 335
His Gly Thr Val Val Leu Glu Leu Gln Tyr Thr Gly Thr Asp Gly Pro
            340                 345                 350
Cys Lys Val Pro Ile Ser Ser Val Ala Ser Leu Asn Asp Leu Thr Pro
        355                 360                 365
Val Gly Arg Leu Val Thr Val Asn Pro Phe Val Ser Val Ala Thr Ala
    370                 375                 380
Asn Ala Lys Val Leu Ile Glu Leu Glu Pro Pro Phe Gly Asp Ser Tyr
385                 390                 395                 400
Ile Val Val Gly Arg Gly Glu Gln Gln Ile Asn His His Trp His Lys
                405                 410                 415
Ser Gly Ser Ser Ile Gly Lys Ala Phe Thr Thr Thr Leu Lys Gly Ala
            420                 425                 430
Gln Arg Leu Ala Ala Leu Gly Asp Thr Ala Trp Asp Phe Gly Ser Val
        435                 440                 445
Gly Gly Val Phe Thr Ser Val Gly Lys Ala Val
    450                 455

<210> SEQ ID NO 18
<211> LENGTH: 33
<212> TYPE: DNA
<213> ORGANISM: ARTIFICIAL SEQUENCE
<220> FEATURE:
<223> OTHER INFORMATION: primer

<400> SEQUENCE: 18
tatcgtacga tgagagttgt gtttgtcgtg cta                              33

<210> SEQ ID NO 19
<211> LENGTH: 31
<212> TYPE: DNA
<213> ORGANISM: ARTIFICIAL SEQUENCE
<220> FEATURE:
<223> OTHER INFORMATION: primer

<400> SEQUENCE: 19
```

```
atagcgcgct tagacagccc ttcccaactg a                                    31
```

<210> SEQ ID NO 20
<211> LENGTH: 27
<212> TYPE: DNA
<213> ORGANISM: ARTIFICIAL SEQUENCE
<220> FEATURE:
<223> OTHER INFORMATION: LTR-FL probe

<400> SEQUENCE: 20

```
cacaacagac gggcacacac tacttga                                         27
```

<210> SEQ ID NO 21
<211> LENGTH: 25
<212> TYPE: DNA
<213> ORGANISM: ARTIFICIAL SEQUENCE
<220> FEATURE:
<223> OTHER INFORMATION: LTR-LC probe

<400> SEQUENCE: 21

```
cactcaaggc aagctttatt gaggc                                           25
```

<210> SEQ ID NO 22
<211> LENGTH: 25
<212> TYPE: DNA
<213> ORGANISM: ARTIFICIAL SEQUENCE
<220> FEATURE:
<223> OTHER INFORMATION: AA55M primer

<400> SEQUENCE: 22

```
gctagagatt ttccacactg actaa                                           25
```

<210> SEQ ID NO 23
<211> LENGTH: 21
<212> TYPE: DNA
<213> ORGANISM: ARTIFICIAL SEQUENCE
<220> FEATURE:
<223> OTHER INFORMATION: M667 primer

<400> SEQUENCE: 23

```
ggctaactag ggaacccact g                                               21
```

<210> SEQ ID NO 24
<211> LENGTH: 34
<212> TYPE: DNA
<213> ORGANISM: ARTIFICIAL SEQUENCE
<220> FEATURE:
<223> OTHER INFORMATION: CD3-P1 probe

<400> SEQUENCE: 24

```
ggctgaaggt tagggatacc aatattcctg tctc                                 34
```

<210> SEQ ID NO 25
<211> LENGTH: 30
<212> TYPE: DNA
<213> ORGANISM: ARTIFICIAL SEQUENCE
<220> FEATURE:
<223> OTHER INFORMATION: CD3-P2 probe

<400> SEQUENCE: 25

```
ctagtgatgg gctcttccct tgagcccttc                                      30
```

<210> SEQ ID NO 26
<211> LENGTH: 23
<212> TYPE: DNA
<213> ORGANISM: ARTIFICIAL SEQUENCE
<220> FEATURE:

```
<223> OTHER INFORMATION: CD3-in-F primer

<400> SEQUENCE: 26
ggctatcatt cttcttcaag gta                                              23

<210> SEQ ID NO 27
<211> LENGTH: 22
<212> TYPE: DNA
<213> ORGANISM: ARTIFICIAL SEQUENCE
<220> FEATURE:
<223> OTHER INFORMATION: CD3-in-R primer

<400> SEQUENCE: 27
cctctcttca gccatttaag ta                                               22
```